(12) United States Patent
O'Connor et al.

(10) Patent No.: US 9,138,456 B2
(45) Date of Patent: Sep. 22, 2015

(54) LIPOPEPTIDE COMPOSITIONS AND RELATED METHODS

(71) Applicant: Cubist Pharmaceuticals, Inc., Lexington, MA (US)

(72) Inventors: Sandra O'Connor, Hudson, NH (US); Sophie Sun, Lexington, MA (US); Gaauri Naik, Cambridge, MA (US)

(73) Assignee: Cubist Pharmaceuticals LLC, Kenilworth, NJ (US)

( * ) Notice: Subject to any disclaimer, the term of this patent is extended or adjusted under 35 U.S.C. 154(b) by 0 days.

(21) Appl. No.: 14/096,346

(22) Filed: Dec. 4, 2013

(65) Prior Publication Data

US 2014/0364380 A1 Dec. 11, 2014

Related U.S. Application Data

(62) Division of application No. 13/511,246, filed as application No. PCT/US2010/057910 on Nov. 23, 2010, now Pat. No. 8,835,382.

(60) Provisional application No. 61/263,784, filed on Nov. 23, 2009.

(51) Int. Cl.
*A61K 38/12* (2006.01)
*C07K 7/50* (2006.01)
*A61K 9/00* (2006.01)
*A61K 9/19* (2006.01)
*A61K 47/26* (2006.01)
*A61K 38/10* (2006.01)
A61K 9/08 (2006.01)
A61K 38/00 (2006.01)
C07K 11/02 (2006.01)

(52) U.S. Cl.
CPC .............. *A61K 38/12* (2013.01); *A61K 9/0019* (2013.01); *A61K 9/19* (2013.01); *A61K 38/10* (2013.01); *A61K 47/26* (2013.01); A61K 9/00 (2013.01); A61K 9/08 (2013.01); A61K 38/00 (2013.01); *C07K 11/02* (2013.01)

(58) Field of Classification Search
CPC ......... A61K 9/0019; A61K 9/08; A61K 9/19; A61K 38/00; A61K 47/26; A61K 9/00; A61K 38/10; A61K 38/12; C07K 11/02
See application file for complete search history.

(56) References Cited

U.S. PATENT DOCUMENTS

| | | | |
|---|---|---|---|
| 4,331,594 A | 5/1982 | Hamill et al. | |
| 4,439,425 A | 3/1984 | Tarcsay et al. | |
| 4,482,487 A | 11/1984 | Abbott et al. | |
| 4,537,717 A | 8/1985 | Abbott et al. | |
| 4,874,843 A | 10/1989 | Baker et al. | |
| 4,882,164 A | 11/1989 | Ferro | |
| 5,271,935 A | 12/1993 | Franco et al. | |
| 5,336,756 A | 8/1994 | Schwartz et al. | |
| 5,387,670 A | 2/1995 | Roy et al. | |
| 5,629,288 A | 5/1997 | Lattrell et al. | |
| 5,912,226 A | 6/1999 | Baker et al. | |
| 5,955,509 A | 9/1999 | Webber et al. | |
| 6,194,383 B1 | 2/2001 | Hammann et al. | |
| 6,468,967 B1 | 10/2002 | Oleson et al. | |
| 6,696,412 B1 | 2/2004 | Kelleher | |
| 6,716,962 B2 | 4/2004 | Borders et al. | |
| 6,852,689 B2 | 2/2005 | Oleson et al. | |
| RE39,071 E | 4/2006 | Baker et al. | |
| 7,138,487 B2 | 11/2006 | Borders et al. | |
| 7,279,597 B1 | 10/2007 | Leone-Bay et al. | |
| 8,003,673 B2 | 8/2011 | Alder et al. | |
| 8,058,238 B2 | 11/2011 | Kelleher et al. | |
| 8,129,342 B2 | 3/2012 | Kelleher | |
| 8,309,061 B2 | 11/2012 | Chaudry | |
| 8,431,539 B2 | 4/2013 | Palepu et al. | |
| 8,604,164 B2 | 12/2013 | Kelleher et al. | |
| 8,835,382 B2 | 9/2014 | O'Connor et al. | |
| 2002/0111311 A1 | 8/2002 | Govardhan et al. | |
| 2002/0132762 A1 | 9/2002 | Borders | |
| 2003/0045484 A1 | 3/2003 | Keith | |
| 2003/0045678 A1 | 3/2003 | Keith | |
| 2004/0067878 A1 | 4/2004 | Hill | |
| 2004/0077601 A1 | 4/2004 | Adams | |
| 2004/0242467 A1 | 12/2004 | Borders | |
| 2005/0009747 A1 | 1/2005 | Kelleher | |
| 2005/0027113 A1 | 2/2005 | Miao et al. | |
| 2005/0152979 A1 | 7/2005 | Besman et al. | |
| 2005/0196418 A1 | 9/2005 | Yu | |

(Continued)

FOREIGN PATENT DOCUMENTS

CA 2675622 A1 8/2008
CN 1592753 A 3/2005

(Continued)

OTHER PUBLICATIONS

Food source of lactose, from Dietitians of Canada, pp. 1-3, published in 2013.*
Source of sucrose, from http://www.ehow.com/about_5376127_sources-sucrose.html, pp. 1-2, accessed Nov. 7, 2014.*
Mannitol, from http://www.drugs.com/inactive/mannito1-142.html?printable=1, pp. 1-2, accessed Nov. 7, 2014.*
Richards et al, Trehalose: a review of properties, history of use and human tolerance, and results of multiple safety studies, Food and Chemical Toxicology, 2002, 40, pp. 871-898.*
Water, from http://www.biology-online.org/dictionary/Water, pp. 1-3, accessed Apr. 24, 2014.*
Sun et al., "Development of an Improved Daptomycin Drug Product: Immediate Reconstitution, Room Temperature Product Stability and Reconstitution Stability", AAPS 2011, Abstract for Poster No. T3328 Published Abstract: http://abstracts.aaps.org/SecureView/AAPSJournal/vmqutdm9e488ov6bhOqy.pdf.

(Continued)

*Primary Examiner* — Julie Ha
*Assistant Examiner* — Li Ni Komatsu
(74) *Attorney, Agent, or Firm* — Dianne Pecoraro; Laura M. Ginkel

(57) ABSTRACT

The present disclosure provides novel powder daptomycin formulations which have improved chemical stability and faster reconstitution times when in the solid state. Some examples of the compositions comprise daptomycin and sucrose.

15 Claims, 22 Drawing Sheets

(56) References Cited

U.S. PATENT DOCUMENTS

| | | | |
|---|---|---|---|
| 2006/0014674 | A1 | 1/2006 | Keith |
| 2006/0018933 | A1 | 1/2006 | Vaya |
| 2006/0018934 | A1 | 1/2006 | Vaya |
| 2006/0024365 | A1 | 2/2006 | Vaya |
| 2006/0264513 | A1 | 11/2006 | Leone-Bay et al. |
| 2006/0269485 | A1 | 11/2006 | Friedman |
| 2007/0116729 | A1 | 5/2007 | Palepu |
| 2007/0128694 | A1 | 6/2007 | Baltz et al. |
| 2007/0191280 | A1 | 8/2007 | Kelleher |
| 2008/0220441 | A1 | 9/2008 | Birnbaum |
| 2009/0197799 | A1 | 8/2009 | Keith |
| 2010/0041589 | A2 | 2/2010 | Keith et al. |
| 2011/0124551 | A1 | 5/2011 | Palepu et al. |
| 2011/0172167 | A1 | 7/2011 | Palepu et al. |
| 2011/0207658 | A1 | 8/2011 | Kelleher |
| 2012/0149062 | A1 | 6/2012 | Kelleher et al. |
| 2012/0270772 | A1 | 10/2012 | O'Conner |
| 2013/0280760 | A1 | 10/2013 | Kelleher et al. |

FOREIGN PATENT DOCUMENTS

| | | |
|---|---|---|
| CN | 1616083 A | 5/2005 |
| CN | 101330905 A | 12/2008 |
| EP | 0178152 | 4/1986 |
| EP | 0294990 | 12/1988 |
| EP | 0386951 A2 | 3/1989 |
| EP | 0511866 | 11/1992 |
| EP | 0521408 | 1/1993 |
| EP | 0629636 | 12/1994 |
| EP | 1252179 | 10/2002 |
| JP | 64047388 | 2/1989 |
| JP | 04224197 | 8/1992 |
| JP | H05-194257 A | 8/1993 |
| JP | 05239090 | 9/1993 |
| JP | 05271284 | 10/1993 |
| JP | H10-212241 A | 8/1998 |
| JP | 2003-095975 A | 4/2003 |
| JP | 2005-060377 A | 3/2005 |
| WO | 93/10809 A1 | 6/1993 |
| WO | WO9321207 | 10/1993 |
| WO | 97/45135 A1 | 12/1997 |
| WO | WO9927954 | 6/1999 |
| WO | WO 9927957 | 6/1999 |
| WO | WO 9940113 | 8/1999 |
| WO | WO9943700 | 9/1999 |
| WO | WO 0018419 | 4/2000 |
| WO | WO01/44274 A1 | 6/2001 |
| WO | WO 01/53330 | 7/2001 |
| WO | WO01/53330 A2 | 7/2001 |
| WO | WO0153330 | 7/2001 |
| WO | WO02/055537 A1 | 7/2002 |
| WO | WO02/056829 A2 | 7/2002 |
| WO | WO02/059145 A1 | 8/2002 |
| WO | WO02059145 | 8/2002 |
| WO | WO02/096936 A2 | 12/2002 |
| WO | WO02096936 | 12/2002 |
| WO | WO2004/004658 A2 | 1/2004 |
| WO | WO2006/084174 A2 | 8/2006 |
| WO | WO2006/084174 A3 | 8/2006 |
| WO | WO2007/061529 A1 | 5/2007 |
| WO | WO2007/099396 A2 | 9/2007 |
| WO | WO2007/099396 A3 | 9/2007 |
| WO | 2008/102849 A1 | 8/2008 |
| WO | WO2008/127291 A2 | 10/2008 |
| WO | WO2008/127291 A3 | 10/2008 |
| WO | 2008/150479 A2 | 12/2008 |
| WO | WO2009144739 A1 | 12/2009 |
| WO | WO2011/019839 A2 | 2/2011 |
| WO | WO2011/035108 A1 | 3/2011 |
| WO | WO2011/062676 A1 | 5/2011 |
| WO | WO2011/063419 A2 | 5/2011 |
| WO | WO2012/061360 A2 | 5/2012 |
| WO | WO2012/088441 A1 | 6/2012 |
| WO | WO2012/112319 A1 | 8/2012 |

OTHER PUBLICATIONS

Horowitz et al., Isolation and Characterization of a Surfactant Produced by *Bacillus licheniformis* 86; Journal of Industrial Microbiology 1990, vol. 6, pp. 243-248.

Fostel, et al., "Emerging Novel Antifungal Agents," DDT; vol. 5; No. 1; Jan. 2000; pp. 25-32.

Caballero Granado et al.; Case-control Study of Risk Factors for the Development of Enterococcal Bacteremia; Eur. J. Clin. Microbiol. Infect. Dis. 2001, vol. 20, p. 83-90.

Desai et al., Microbial Production of Surfactants and Their Commercial Potential; Microbiology and Molecular Biology Reviews 1997, vol. 61, pp. 47-64.

Debruin. Michael F., Efficacy and safety of daptomycin for the treatment of bacteremia and serious infections due to gram-positive bacteria; 4th Decennial International Conference on Nosocomial and Healthcare-Associated Infections; Poster #594 P-S2-37 (Mar. 5-9, 2000), 14 pages.

Amorij: Development of Stable Influenza Vaccine Powder Formulations: challenges and possibilities, Pharmaceutical Research, 2008, 25:1256-1273.

Cubicin label, Aug. 2010.

Notification of Transmittal of International Preliminary Report on Patentability in International Application No. PCT/US2010/057910, mailed May 24, 2012, 7 pages.

International Search Report and Written Opinion dated Aug. 22, 2011 in international application No. PCT/US2010/057910, 15 pages.

pH-water quality, from http://extension.usu.edu/waterquality/htm/whats-in-your-water/ph, pp. 1-2, accessed Jul. 23, 2013.

Smales et al, Therapeutic proteins, methods and protocols, Humana press, 2005, pp. 287-292.

Wang, Lyophilization and development of solid protein pharmaceuticals, International Journal of Pharmaceutics, 2000, 203, pp. 1-60.

Machine translation of CN 1616083 A, pp. 1-9, publication date May 18, 2005.

Haworth et al.; *Staphylococcus aureus* ventriculitis treated with single-dose intraventricular vancomycin or daptomycin (LY146032): bacterial and antibiotic kinetics in hydrocephalic rabbits; Antimicrobial Agents and Chemotherapy 1990, vol. 34, pp. 245-251.

Jancarik et al., Sparse matrix sampling: a screening method for crystallization of proteins, J Appl. Cryst., 1991, vol. 24, pp. 409-411.

Johnson et al., ICAA 1987, poster 161, 1 page.

Katz et al., A pilot study of high-dose short duration daptomycin for the treatment of patients with complicated skin and skin structure infections caused by gram-positive bacteria, International Journal of Clinical Practice, 2008, pp. 1-10.

LeClercq et al., Effects of Combinations of Beta-Lactams, Daptomycin, Gentamicin and Glycopeptides against Glycopeptide-Resistant *Enterococci*; Antimicrobial Agents and Chemotherapy, 1991, vol. 35, pp. 92-98.

Louie et al., Comparison of in vitro inhibitory and Bactericial Activities of Daptomycin (LY 146032) and Four Reference Antibiotics, Singly and in Combination, against Gentamicin-Susceptible and High-Level-Gentamicin-Resistant *Enterococci*; Chemotherapy; 1993, vol. 39, pp. 302-310.

Luu et al., Treatment of Chronic Experimental *Staphylococcus aureus* Osteomyelitis with LY 146032 and Vancomycin; Eur. J. Clin. Microbiol. Infect. Dis. 1989, vol. 8, pp. 562-563.

Mader et al., Comparative Evalulation of Daptomycin (LY146032) and comycin in the Treatment of Experimental Methicillin-Resistant *Staphylococcus aureus* Osteomyelitis in Rabbits; Comparative Evaluation of Daptomycin Antimicrobial Agents and Chemotherapy, 1989, vol. 33, pp. 689-692.

Mariani et al., Development of decreased susceptibility to daptomycin and vancomycin in a *Staphylococcus aureus* strain during prolonged therapy; Journal of Antimicrobial Chemotherapy 2013, p. 481-83.

Mathews et al., IDSA poster, 2001.

Mchenney et al., Molecular Cloning and Physical Mapping of the Daptomycin Gene Cluster from *Streptomyces roseosporus*; Journal of Bacteriology, 1998, vol. 180, pp. 143-151.

Mobarakai et al., Bactericidal Activities of Peptide Antibiotics against Multidrug-Resistant *Enterococcus faecium*; Antimicrobial

(56) References Cited

OTHER PUBLICATIONS

Agents and Chemotherapy; 1994, vol. 38, pp. 385-387.
Moise et al., susceptibility relationship between vancomycin and daptomycin in *Staphylococcus aureus*: facts and assumptions; Lancet Infect. Dis. 2009, vol. 9, pp. 617-624.
Patel et al., An Association bettween Reduced Susceptibility to Daptomycin and Reduced Susceptibility to Vancomycin in *Staphylococcus aureus*; Clinical Infectious Diseases: Correspondence to the Editor; Jun. 1, 2006, vol. 42, pp. 1652-1653.
Sader et al., Nine-Hospital Study Comparing Broth Microdilution and Etest method Results for Vaqncomycin and Daptomycin against Methicillin-Resistant *Staphylococcus aureus*; Antimicrobial Agents and Chemotherapy, 2009, vol. 53, pp. 3162-3165.
Sader et al., Update on the In Vitro Activity of Daptomycin Tested against 17,193 Gram-positive Bacteria Isolated from European Medical Centers (2005-2007); Journal of Chemotherapy 2009, vol. 21, pp. 500-506.
Sakoulas et al., Clinical Outcomes of Patients Receiving Daptomycin for the Treatment of *Staphylococcus aureus* Infections and Assessment of Clinical Factors for Daptomycin Failure: A Retrospective Cohort Study Tuilizing the Cubicin Outcomes Registry and Experience; Clinical Therapeutics, 2009, vol. 31, pp. 1936-1945.
Sapico et al., 146032, Alone nad in Combination with Gentamicin, for the Treatment of Enterococcal Pyelonephritis in the Rat Model; Antimicrobial Agents and Chemotherapy 1988, vol. 32, pp. 81-83.
Silva et al., In Vitro Activity of LY146032 Against Gram-Positive Bacteria; Diagn. Microbiol. Infect. Dis., 1988, vol. 9, pp. 79-85.
Silverman et al., Inhibition of Daptomycin by Pulmonary Surfactant: In Vitro Modeling and Clinical Impact; The Journal of Infectious Disease; 2005, vol. 191, pp. 2149-2152.
Silverman et al., Resistance Studies with Daptomycin; Antimicrobial Agents and Chemotherapy; 2001, vol. 45, pp. 1799-1802.
Snydman et al., Comparative In Virro Activities of Daptomycin and Vancomycin against Resistant Gram-Positive Pathogens; Antimicrobial Agents and Chemotherapy; 2000, vol. 44, pp. 3447-3450.
Steenbergen et al., Daptomycin: a lipopeptide antibiotic for the treatment of serious Gram-Positive infections; Journal of Antimicrobial Chemotherapy, 2005, vol. 55, pp. 283-288.
Stratton et al., Bactericidal Activity of Deptomycin (LY146032) Compared with Those of Ciprofloxacin, Vancomycin, and Ampicillin against *Enterocci* as Determined by Kill-Kinetic Studies; Antimicrobial Agents and Chemotherapy 1987, vol. 31, pp. 1014-1016.
U.S. Appl. No. 10/024,405 (Abandoned), filed Dec. 18, 2001.
Tenover et al., Characterisation of a *Staphylococcus aureus* strain with progressive loss of susceptibility to vancomycin and daptomycin during therapy; International Journal of Antimicrobial Agents; 2009, p. 564-68.
Thibault et al., Attenuation by Daptomycin of Gentamicin-Induced Experimental Nephrotoxicity; Antimicrobial Agents and Chemotherapy; 1994, vol. 38, pp. 1027-1035.
Woodworth et al., Tobramycin and daptomycin disposition when co-administered to healthy volunteers; Journal of Antimicrobial Chemotherapy, 1994, vol. 33 pp. 655-659.
U.S. Appl. No. 61/243,402, filed Sep. 17, 2009 (Priority Document for WO2011035108).
U.S. Appl. No. 61/263,695, filed Nov. 23, 2009 (Priority Document for WO2011035108 and WO2011062676).
U.S. Appl. No. 61/371,802, filed Aug. 9, 2010 (Priority Document for WO2011062676).
*Cubist Pharmaceutical, Inc. v. Hospira, Inc.*, No. 1:12cv367 (D. Mass. Filed Mar. 21, 2012) (Def. Hospira, Inc. Preliminary Invalidity Contentions).
Supplementary European Search Report PCT/US2010057910 Dated Feb. 28, 2014. 8 Pages.
Debono: Enzymatic and Chemical Modifications of Lipopeptide Antibiotic A21978C: The Synthesis and Evaluation of Daptomycin (LY146032), The Journal of Antibiotics, 1988, 41(8):1093-1105.
Miao et al., "Daptomycin biosynthesis in *Streptomyces roseosporus*: cloning and analysis of the gene cluster and revision of peptide stereochemistry," Microbiology 2005, vol. 151 (5), 1507-23.

Debono, et al., "A21978C, A Complex of New Acidic Peptide Antibiotics: Isolation, Chemistry, and Mass Spectral Structure Elucidation," The Journal of Antibiotics 1987, vol. XL (6), p. 761-77.
Lodish et al., Molecular Cell Biology (ed. by J. Darnell, H. Lodish, and D. Baltimore, Scientific American Books, Inc., New York: 1986), Chapter 3, p. 53.
Woodworth et al., "Single-Dose Pharmacokinetics and Antibacterial Activity of Daptomycin, a New Lipopeptide Antibiotic, in Healthy Volunteers," Antimicrobial Agent and Chemotherapy 1992, vol. 36, p. 318-25.
McKindley et al., "Drug Use in the Critically Ill Patient with Renal Dysfunction-Application of the DREM System," Infectious Diseases in Critical Care Medicine Biotechnology of Antibiotics (ed. B.A. Cunha, New York: Marcel Dekker, Inc., 1998) Chapter 41, pp. 781-801.
Tally et al., Daptomycin: a novel agent for Gram-positive infections; Expert Opinion. on Investigational Drugs; 1999, vol. 8, pp. 1223-1238.
Janson et al., Protein Purification: Principles, High Resolution Methods, and Applications; Ch. 1: Introduction to Protein Purification; John Wiley & Sons, Inc., 1998; pp. 3-48, p. 80, and pp. 125-126.
Lin et al., "Recovery and Purification of the Lipopeptide Biosurfactant of *Bacillus subtilis* by Ultrafiltration," Biotechnology Techniques, 1997, vol. 11, p. 413-16.
Shaw, D.J., "Liquid-Gas and Liquid-Liquid Interfaces," Introduction to Colloid and Surface Chemistry, Butterworth-Heinemann Ltd.,1989, pp. 49-90.
Kirsch, et al., "Kinetics of the Aspartyl Transpeptidation of Daptomycin, a Novel Lipopeptide Antibiotic," Pharmaceutical Research; 1989, vol. 6, p. 387-93.
Remington: The Science and Practice of Pharmacy, (19th edition, Mack Publishing Company, 1985), pp. 539-551, 1529-1530, 1549-1550, and 1558.
Sexton D. et al., "The Use of Daptomycin, a Lipopeptide Antibiotic, in the Treatment of Gram Positive Infections in Man," Interscience Conference on Antimicrobial Agents and Chemotherapy 1988, Abstract No. 932.
Selwyn, et al.; Infections (Excluding AIDS) of Injection Drug Users; Harrison's Principles of Internal Medicine; Fauci, et al. eds., 14th ed., McGraw-Hill, 1998, pp. 831-832, and 847.
Lee et al., Program and Abstracts of the ICAAC 1991, Abstract No. 865.
Rotschafer et al., "Therapeutic Update on Clycopeptide and Lipopeptide Antibiotics," Pharmacotherapy 1988, vol. 8, 211-19.
Mutschler et al., Drug Actions: Basic Principles and Therapeutic Aspects; Ch. 2: Pharmacokinetics; Medpharm Scientific Publishers, Stuttgart, Germany (1995); p. 5, 47 pages.
Freeman et al., Once-daily Dosing of Aminoglycosides: Review and Recommendations for Clinical Practice; J. Antimicr. Chemother. 1997, vol. 39, p. 677-86.
Ebert et al., Pharmacodynamics Properties of Antibiotics: Application to Drug Monitoring and Dosage Regimen Design; Infection Control and Hospital Epidemiology; 1990, 11(6), pp. 319-326.
Barclay et al., What is the Evidence for Once-Daily Aminoglycoside Therapy; Clin. Pharmacokinetics. 1994, 27(i), pp. 32-48.
Baltz, "Lipopeptide Antibiotics Produced by *Streptomyces roseosporus* and *Streptomyces fradiae*," Biotechnology of Antibiotics 1997, 2d ed.; pp. 415-435.
Craig, "Once-daily versus multiple-daily dosing of aminoglycosides," J Chemother.; 1995, vol. 7 (Suppl 2), pp. 47-52.
Schnellmann et al.; Cassarett and Douls Toxicology: The Basic Science of Poisons; Chapter 14: Toxic Responses of the Kidney; (5th ed.) (1996), pp. 491-514.
Benoit et al. "Destruction and regeneration of skeletal muscle after treatment with a local anesthetic, bupivacaine (Marcaine®)," J Anat. 1970, vol. 107, pp. 547-556.
Cubist Pharmaceuticals, Press Release, Feb. 5, 2008, Lexington, MA.
U.S. Appl. No. 07/060,148, filed Jun. 10, 1987; File History; Abandoned.
Akins et al., In Vitro Activities of Daptomycin, Arbekacin, Vancomycin, and Gentamicin Alone and/or in Combination against

(56) References Cited

OTHER PUBLICATIONS

Glycopeptide Intermediate-Resistant *Staphylococcus aureus* in an Infection Model; Antimicrobial Agents and Chemotherapy; 2000, vol. 44, pp. 1925-1929.

Akins et al.; Bactericidal Activities of Two Daptomycin Regimens against Clinical Strains Glycopeptide Intermediate-Resistant *Staphylococcus aureus*, Vancomycin-Resistant *Enterococcus faccium*, and Methicillin-Resistant *Staphylococcus aureus* Isolates in an In Vitro Pharmacodynamic Model with Simulated Endocardial Vegetations; Antimicrobial Agents and Chemotherapy; 2001, vol. 45, pp. 454-459.

Arbeit et al., The Safety and Efficacy of Daptomycin for the Treatment of Complicated Skin and Skin-Structure Infections; Clinical Infectious Diseases; 2004, vol. 38, pp. 1673-1681.

Auwera et al., Ex-vivo study of serum bactericidal titers and kiilling rates of daptomycin (LY146032) combined or not combined with amikacin compared with those of vancomycin; Antimicrobial Agents and Chemotherapy; 1989, vol. 33, pp. 1783-1790.

Barry et al., In vitro activities of daptomycin against 2,789 clinical isolates from 11 North American Medical Centers; Antimicrobial Agents and Chemotherapy; 2001, vol. 45, pp. 1919-1922.

Benvenuto et al., Pharmacokinetics and Tolerability of Daptomycin at Doses up to 12 Milligrams per Kilogram of Body Weight Once Daily in Healthy Volunteers; Antimicrobial Agents and Chemotherapy; 2006, vol. 50, pp. 3245-3249.

Dvorchik et al., Daptomycin Pharmacokinetics and Safety following Administration of Escalating Doses Once Daily to Healthy Subjects; Antimicrobial Agents and Chemotherapy; 2003, vol. 47, pp. 1318-1323.

Bingen et al., Bactericidal activity of Fancomycin, Daptomycin, Ampicillin and Aminoglycosides against Vancomycin-resistant *Enterecoccus*; J of Antimicrobial Chemotherapy; 1990, vol. 26, pp. 619-626.

Bryant et al., Effect of Abscess Milieu on Bactericidal Activity of IX146032 against *Staphylococci*; Eur. J. Clin. Microbiol.; 1987, vol. 6, pp. 186-188.

Caballero_Granado et al.; Case-control Study of Risk Factors for the Development of Enterococcal Bacteremia; Eur. J. Clin. Microbiol. Infect. Dis. 2001, vol. 20, p. 83-90.

Caron et al.; Daptomycin or teicoplanin in combination with gentamicin for treatment of experiemental endocarditis due to highly glycopeptide-resistant isolate of *Enterococcus faecium*; Antimicrobial Agents and Chemotherapy; 1992, vol. 36, pp. 2611-2616.

Carter et al., Protein Crystallization Using Incomplete Factorial Experiments; J. Biol. Chem., 1979, vol. 254, pp. 12219-12223.

Chaftari et al.; Efficacy and safety of daptomycin in the treatment of Gram-positive catheter-related bloodstream infections in cancer patients; International Journal of Antimicrobial Agents; 2010, vol. 36, pp. 182-186.

Chayen et al.; Recent advances in methodology for the crystallization of biological macromolecules; Journal of Crystal Growth; 1999, pp. 649-655.

Crompton et al., Outocmes with daptomycin in the treatment of *Staphylococcus aureus* infections with a range of vancomycin MICs; Journal of Antimicrobial Chemotherapy; 2010, vol. 65, pp. 1784-1791.

Cubicin label, Nov. 2011; 34 pages.

Cui et al., Correlation between Reduced Daptomycin Susceptibility and Vancomycin Resistance in Vancomycin-Intermediate *Staphylococcus aureus*; Antimicrobial Agents and Chemotherapy; 2006, vol. 50, pp. 1079-1082.

Cunha et al., Daptomycin resistance and treatment failure following vancomycin for methicillin-resistant *Staphylococcus aureus* (MRSA) mitral valve acute bacterial endocarditis (ABE); Eur. J. Clin. Microbiol. Infect. Dis.; 2009, vol. 28, pp. 831-833.

Davis et al., Daptomycin versus Vancomycin for Complicated Skin and Skin Structure Infections: Clinical and Economic Outcomes, Pharmacotherapy, 2007, vol. 27, pp. 1611-1618.

Debbia et al., In Vitro Activity of LY146032 Alone and in Combination with Other Antibiotics against Gram-Positive Bacteria, Antimicrobial Agents and Chemotherapy, 1988, vol. 32, pp. 279-281.

El-Mady et al., The Bactericidal Activity of Ampicillin, Daptomycin, and Vancomycin Against Ampicillin-Resistant *Enterococcus faecium*, Diagn. Micro. Inf. Dis., 1991, vol. 14, pp. 141-145.

Evdokimov et al., Overproduction, purification, crystallization and preliminary X-ray diffraction analysis of YopM, an essential virulence factor extruded by the plague bacterium *Yersinia pestis*, Acta Crystallographica, 2000, vol. 56, pp. 1676-1679.

DuCruix, et al., Crystallization of Nucleic acids and Proteins, A Practical Approach, 2d ed., 1999, pp. 92-95, 4 pages.

Forward et al., Comparative activity of daptomycin and teicoplanin against *Enterococci* isolated from blood and urine, Can. J. Infect. Dis., 1992, vol. 3, pp. 173-178.

Fowler et al., Daptomycin versus Standard Therapy for Bacteremia and Endocarditis Caused by *Staphylococcus aureus*, The New England Journal of Medicine, 2006, vol. 355, pp. 653-665.

"Cubicin: EPAR—Scientific Discussion", EMEA, 2006. [online]. [Published on Internet Nov. 8, 2006]. <URL: http://www.ema.europa.eu/docs/en_GB/_ibrary/EPAR_-_Scientific_Discussion/human/000637/WC500036046.pdf>.

"Protein structure," from http://www.sciencedaily.com/articles/p/protein_structure.htm, pp. 1-3, accessed Feb. 11, 2015.

Notice of Reasons for Rejection, mailed Nov. 19, 2014 in Japanese Patent Application No. 2012-540161, 5 pages (English translation).

English translation of Chinese Patent Application Publication No. 1616083 (published May 18, 2005) as cited in the Japanese Notice of Reasons for Rejection, mailed Nov. 19, 2014 in Japanese Patent Application No. 2012-540161, 4 pages.

\* cited by examiner

Daptomycin

"anhydro-daptomycin"

"β-isomer" or "β-isomer of daptomycin"

lactone hydrolysis product

Table 6

| No. | Liquid Formulation Components | Recon Time (min) | Formulation (%w/v in solution) | Formulation (solid state) 500 mg/vial | Ratios Dap : sugar Dap : PO4 Dap : Mannitol | Molar Ratio Dap : Sugar(s) |
|---|---|---|---|---|---|---|
| 0 | Daptomycin, 50 mm PO4, pH 7.0 | 1.4 min | | 500mg Dap | | |
| 1 | 2.5% Trehalose, 50mM PO4, pH 7.0 | <1 | 10.5% Dap 2.5% Trehalose 0.71% PO4 | 500mg Dap 119mg Tre 35.5mg PO4 | 1:0.24 1:0.071 | 1:2.13 1:0.81 |
| 2 | 5 % Trehalose, 50mM PO4, pH 7.0 | <1 | 10.5% Dap 5% Trehalose 0.71% PO4 | 500mg Dap 238mg Tre 35.5mg PO4 | 1:0.48 1:0.071 | 1:4.26 1:0.81 |
| 3 | 10 % Trehalose, 50mM PO4, pH 7.0 | <1 | 10.5% Dap 10% Trehalose 0.71% PO4 | 500mg Dap 476.2mg Tre 35.5mg PO4 | 1:0.95 1:0.071 | 1:8.52 1:0.81 |
| 4 | 2.5% Sucrose, 50mM PO4, pH 7.0 | <1 | 10.5% Dap 2.5% Sucrose 0.71% PO4 | 500mg Dap 119mg Sucrose 35.5mg PO4 | 1:0.24 1:0.071 | 1:1.12 1:0.81 |
| 5 | 5 % Sucrose, 50mM PO4, pH 7.0 | <1 | 10.5% Dap 5% Sucrose 0.71% PO4 | 500mg Dap 238mg Sucrose 35.5mg PO4 | 1:0.48 1:0.071 | 1:2.24 1:0.81 |
| 6 | 10 % Sucrose, 50mM PO4, pH 7.0 | <1 | 10.5% Dap 10% Sucrose 0.71% PO4 | 500mg Dap 476.2mg Suc 35.5mg PO4 | 1:0.95 1:0.071 | 1:4.48 1:0.81 |
| 7 | 2.5% Sucrose, 3% Mannitol, 50mM PO4, pH 7.0 | <1 | 10.5% Dap 2.5% Sucrose 3% Mannitol 0.71% PO4 | 500mg Dap 119mg Sucrose 142.9mg Man 35.5mg PO4 | 1:0.24 1:0.29 1:0.071 | 1:1.12 1:2.52 1:0.81 |
| 8 | 5 % Sucrose, 3% Mannitol, 50mM PO4, pH 7.0 | <1 | 10.5% Dap 5% Sucrose 0.71% PO4 | 500mg Dap 238mg Sucrose | 1:0.48 | 1:2.24 |

Fig. 5A

| No. | Liquid Formulation Components | Recon Time (min) | Formulation (%w/v in solution) | Formulation (solid state) 500 mg/vial | Ratios Dap : sugar Dap : PO4 Dap : Mannitol | Molar Ratio Dap : Sugar(s) |
|---|---|---|---|---|---|---|
| 9 | 10 % Sucrose, 3% Mannitol, 50mM PO4, pH 7.0 | <1 | 3% Mannitol 0.71% PO4 | 142.9mg Man 35.5mg PO4 | 1:0.29 1:0.071 | 1:2.52 1:0.81 |
|  |  |  | 10.5% Dap 10% Sucrose 3% Mannitol 0.71% PO4 | 500mg Dap 476.2mg Suc 142.9mg Man 35.5mg PO4 | 1:0.95 1:0.29 1:0.071 | 1:4.48 1:2.52 1:0.81 |
| 10 | 2.5% Sucrose, 6% Mannitol, 50mM PO4, pH 7.0 | <1 | 10.5% Dap 2.5% Sucrose 6% Mannitol 0.71% PO4 | 500mg Dap 119mg Sucrose 285.8 Man 35.5mg PO4 | 1:0.24 1:0.57 1:0.071 | 1:1.12 1:5.04 1:0.81 |
| 11 | 5% Sucrose, 6% Mannitol, 50mM PO4, pH 7.0 | <1 | 10.5% Dap 5% Sucrose 6% Mannitol 0.71% PO4 | 500mg Dap 238.8mg Sucrose 285.8mg Man 35.5mg PO4 | 1:0.48 1:0.57 1:0.071 | 1:2.24 1:5.04 1:0.81 |
| 12 | 10% Sucrose, 6% Mannitol, 50mM PO4, pH 7.0 | <1 | 10.5% Dap 10% Sucrose 6% Mannitol 0.71% PO4 | 500mg Dap 476.2mg Suc 285.8mg Man 35.5mg PO4 | 1:0.95 1:0.57 1:0.071 | 1:4.48 1:5.04 1:0.81 |
| 13 | 20 % Sucrose, 50mM PO4, pH 7.0 | <1 | 10.5% Dap 20% Sucrose 0.71% PO4 | 500mg Dap 952.4mg Suc 35.5mg PO4 | 1:1.90 1:0.071 | 1:8.96 1:0.81 |
| 14 | 25% Trehalose, 50mM PO4, pH 7.0 | <1 | 10.5% Dap 25% Tre 0.71% PO4 | 500mg Dap 1190.5mg Tre 35.5mg PO4 | 1:2.38 1:0.071 | 1:21.32 1:0.81 |
| 15 | 25% Trehalose, pH 4.7 | <1 | 10.5% Dap 25% Tre | 500mg Dap 1190.5mg Tre | 1:2.38 | 1:21.32 |
| 19 | 20% Sucrose, pH 4.7 | <1 | 10.5% Dap 20% Sucrose | 500mg Dap 952.4mg Suc | 1:1.90 | 1:8.96 |

Fig. 5B

| No. | Liquid Formulation Components | Recon Time (min) | Formulation (%w/v in solution) | Formulation (solid state) 500 mg/vial | Ratios Dap : sugar Dap : PO4 Dap : Mannitol | Molar Ratio Dap : Sugar(s) |
|---|---|---|---|---|---|---|
| 23 | 15 % Sucrose, 3% Mannitol, pH 4.7 | 0.3 – 1.5 | 10.5% Dap 15% Sucrose 3% Mannitol | 500mg Dap 750mg Sucrose 142.9mg Man | 1 : 1.5 1 : 0.29 | 1 : 6.73 1 : 2.52 |
| 35 | 20% Lactose, 50 mM PO4, pH 7.0 | <1 | 10.5% Dap 20% Lactose 0.71% PO4 | 500mg Dap 952.4mg Lact 35.5mg PO4 | 1 : 1.90 1 : 0.071 | 1 : 8.80 1 : 0.81 |
| 50 | 2.5% Lactose, 50 mM PO4, pH 7.0 | <1 | 10.5% Dap 2.5% Lactose 0.71% PO4 | 500mg Dap 119mg Lac 35.5mg PO4 | 1 : 0.24 1 : 0.071 | 1 : 1.10 1 : 0.81 |
| 51 | 2.5% Maltose, 50 mM PO4, pH 7.0 | 0.5 – 1.2 | 10.5% Dap 2.5% Maltose 0.71% PO4 | 500mg Dap 119mg Malt 35.5mg PO4 | 1 : 0.24 1 : 0.071 | 1 : 1.12 1 : 0.81 |
| 52 | 2.5% Fructose, 50 mM PO4, pH 7.0 | <1 | 10.5% Dap 2.5% Fructose 0.71% PO4 | 500mg Dap 119mg Fruc 35.5mg PO4 | 1 : 0.24 1 : 0.071 | 1 : 2.13 1 : 0.81 |
| 53 | 2.5% Dextrose, 50 mM PO4, pH 7.0 | 0.6 – 1.1 | 10.5% Dap 2.5% Dextrose 0.71% PO4 | 500mg Dap 119mg Dex 35.5mg PO4 | 1 : 0.24 1 : 0.071 | 1 : 2.13 1 : 0.81 |
| 54 | 2.5%Dextrose/Fructose (1:1), 50mM PO4, pH 7.0 | 0.5 – 1.2 | 10.5% Dap 2.5% Dex/Fruc 0.71% PO4 | 500mg Dap 119mg D/F 35.5mg PO4 | 1 : 0.24 1 : 0.071 | 1 : 1.07 : 1.07 1 : 0.81 |
| 55 | 5% Lactose, 50mM PO4, pH 7.0 | <1 | 10.5% Dap 5% Lactose 0.71% PO4 | 500mg Dap 238mg Lact 35.5mg PO4 | 1 : 0.48 1 : 0.071 | 1 : 2.20 1 : 0.81 |
| 56 | 5% Maltose, 50mM PO4, pH 7.0 | <1 | 10.5% Dap 5% Maltose 0.71% PO4 | 500mg Dap 238mg Malt 35.5mg PO4 | 1 : 0.48 1 : 0.071 | 1 : 2.24 1 : 0.81 |
| 57 | 5% Fructose, 50mM PO4, pH 7.0 | <1 | 10.5% Dap | 500mg Dap | | |

Fig. 5C

| No. | Liquid Formulation Components | Recon Time (min) | Formulation (%w/v in solution) | Formulation (solid state) 500 mg/vial | Ratios Dap : sugar Dap : PO4 Dap : Mannitol | Molar Ratio Dap : Sugar(s) |
|---|---|---|---|---|---|---|
|  |  |  | 5% Fructose 0.71% PO4 | 238mg Fruc 35.5mg PO4 | 1 : 0.48 1 : 0.071 | 1 : 4.26 |
| 58 | 5% Dextrose, 50 mM PO4, pH 7.0 | <1 | 10.5% Dap 5% Dextrose 0.71% PO4 | 500mg Dap 238mg Dex 35.5mg PO4 | 1 : 0.48 1 : 0.071 | 1 : 4.26 1 : 0.81 |
| 59 | 5%Dextrose/Fructose (1:1), 50mM PO4, pH 7.0 | <1 | 10.5% Dap 5% Dex/Fruc 0.71% PO4 | 500mg Dap 238mg D/F 35.5mg PO4 | 1 : 0.48 1 : 0.071 | 1 : 2.13 : 2.13 1 : 0.81 |
| 60 | 2.5% Lactose, pH 4.7 | 1.1 | 10.5% Dap 2.5% Lactose | 500mg Dap 119mg Lac | 1 : 0.24 | 1 : 1.10 |
| 61 | 2.5% Maltose, pH 4.7 | 1.1 | 10.5% Dap 2.5% Maltose | 500mg Dap 119mg Malt | 1 : 0.24 | 1 : 1.12 |
| 62 | 2.5% Fructose, pH 4.7 | 1.2 | 10.5% Dap 2.5% Fructose | 500mg Dap 119mg Fruc | 1 : 0.24 | 1 : 2.03 |
| 64 | 2.5%Dextrose/Fructose (1:1), pH 4.7 | 1.7 | 10.5% Dap 2.5% Dex/Fruc | 500mg Dap 119mg D/F | 1 : 0.24 | 1 : 1.07 : 1.07 |
| 65 | 5% Lactose, pH 4.7 | 1.6 | 10.5% Dap 5% Lactose | 500mg Dap 238mg Lact | 1 : 0.48 | 1 : 2.24 |
| 71 | 6% Mannitol, 50 mM PO4, pH 7.0 | <1 | 10.5% Dap 6% Mannitol 0.71% PO4 | 500mg Dap 285.8mg Man 35.5mg PO4 | 1 : 0.57 1 : 0.071 | 1 : 5.04 1 : 0.81 |
| 73 | 5% Glycine, 50 mM PO4, pH 7.0 | <1 | 10.5% Dap 5% Glycine 0.71% PO4 | 500mg Dap 238mg Glycine 35.5mg PO4 | 1 : 0.48 1 : 0.071 | 1 : 10.31 1 : 0.81 |

Fig. 5D

| No. | Liquid Formulation Components | Recon Time (min) | Formulation (%w/v in solution) | Formulation (solid state) 500 mg/vial | Ratios Dap : sugar Dap : PO4 Dap : Mannitol | Molar Ratio Dap : Sugar(s) |
|---|---|---|---|---|---|---|
| 75 | 15% Sucrose, 50mM PO4, pH 7.0 | <1 | 10.5% Dap 15% Sucrose 0.71% PO4 | 500mg Dap 714.3mg Sucrose 35.5mg PO4 | 1 : 1.5 1 : 0.071 | 1 : 6.73 1 : 0.81 |
| 76 | 15% Sucrose, 50mM PO4, pH 7.0 | <1 | 10.5% Dap 15% Sucrose 0.71% PO4 | 500mg Dap 714.3mg Sucrose 35.5mg PO4 | 1 : 1.5 1 : 0.071 | 1 : 6.73 1 : 0.81 |

Fig. 5E

Table 7

| Formulation ID | Recon Time (min) | Formulation (% w/v in solution) | Formulation (solid state) 500 mg/vial | Ratios Dap : sugar Dap : PO4 Dap : Mannitol | Molar Ratio Dap : Excipients |
|---|---|---|---|---|---|
| 00 | 5 min | Daptomycin, pH 4.7 | 500mg Dap | | |
| 16 | 2 – 4 | 10.5% Dap 2.5% Sucrose | 500mg Dap 119mg Sucrose | 1 : 0.24 | 1 : 1.12 |
| 17 | 0.7 – 2 | 10.5% Dap 5% Sucrose | 500mg Dap 238mg Sucrose | 1 : 0.48 | 1 : 2.24 |
| 18 | 0.3 – 3 | 10.5% Dap 10% Sucrose | 500mg Dap 476.2mg Suc | 1 : 0.95 | 1 : 4.48 |
| 20 | 2 – 8 | 10.5% Dap 2.5% Sucrose 3% Mannitol | 500mg Dap 119mg Sucrose 142.9mg Man | 1 : 0.24 1 : 0.29 | 1 : 1.12 1 : 2.52 |
| 21 | 2 – 6 | 10.5% Dap 5% Sucrose 3% Mannitol | 500mg Dap 238mg Sucrose 142.9mg Man | 1 : 0.48 1 : 0.29 | 1 : 2.24 1 : 2.52 |
| 22 | 0.5 – 2 | 10.5% Dap 10% Sucrose 3% Mannitol | 500mg Dap 476.2mg Suc 142.9mg Man | 1 : 0.95 1 : 0.29 | 1 : 4.48 1 : 2.52 |
| 63 | 2 | 10.5% Dap 2.5% Dextrose | 500mg Dap 119mg Dex | 1 : 0.24 | 1 : 2.13 |

Fig. 6A

| Formulation ID | Recon Time (min) | Formulation (% w/v in solution) | Formulation (solid state) 500 mg/vial | Ratios Dap : sugar Dap : PO4 Dap : Mannitol | Molar Ratio Dap : Excipients |
|---|---|---|---|---|---|
| 66 | 2.4 | 10.5% Dap 5% Maltose | 500mg Dap 238mg Malt | 1:0.48 | 1:2.20 |
| 67 | 2.5 | 10.5% Dap 5% Fructose | 500mg Dap 238mg Fruc | 1:0.48 | 1:4.26 |
| 68 | 2.4 | 10.5% Dap 5% Dextrose | 500mg Dap 238mg Dex | 1:0.48 | 1:4.26 |
| 69 | 2.0 | 10.5% Dap 5% Dex/Fruc | 500mg Dap 238mg D/F | 1:0.48 | 1:2.13 : 2.13 |
| 77 | 3 – 4 | 10.5% Dap 5% Trehalose | 500mg Dap 238mg Tre | 1:0.48 | 1:4.26 |
| | 3 – 5 | 10.5% Dap 2.5% Trehalose | 500mg Dap 119mg Tre | 1:0.24 | 1:2.13 |

Fig. 6B

Table 8

| ID No. | Lipopeptide [A] | Compound [B] | Compound [C] | Buffering Agent [D] | Compounding pH | Molar Ratio of existing components, respectively | Formulation in Solution upon addition of diluent (weight/volume) |
|---|---|---|---|---|---|---|---|
| 1 | daptomycin | Trehalose | | Sodium phosphate dibasic | about 7.0 | 1 : 2.13 : 0.77 | 10.5% Dap 2.5% Trehalose 0.71% Na₂HPO₄ |
| 2 | daptomycin | Trehalose | | Sodium phosphate dibasic | about 7.0 | 1 : 4.26 : 0.77 | 10.5% Dap 5% Trehalose 0.71% Na₂HPO₄ |
| 3 | daptomycin | Trehalose | | Sodium phosphate dibasic | about 7.0 | 1 : 8.53 : 0.77 | 10.5% Dap 10% Trehalose 0.71% Na₂HPO₄ |
| 4 | daptomycin | Sucrose | | Sodium phosphate dibasic | about 7.0 | 1 : 1.12 : 0.77 | 10.5% Dap 2.5% Sucrose 0.71% Na₂HPO₄ |
| 5 | daptomycin | Sucrose | | Sodium phosphate dibasic | about 7.0 | 1 : 2.24 : 0.77 | 10.5% Dap 5% Sucrose 0.71% Na₂HPO₄ |
| 6 | daptomycin | Sucrose | | Sodium phosphate dibasic | about 7.0 | 1 : 4.49 : 0.77 | 10.5% Dap 10% Sucrose 0.71% Na₂HPO₄ |
| 7 | daptomycin | Sucrose | Mannitol | Sodium phosphate dibasic | about 7.0 | 1 : 1.12 : 2.52 : 0.77 | 10.5% Dap 2.5% Sucrose 3% Mannitol 0.71% Na₂HPO₄ |
| 8 | daptomycin | Sucrose | Mannitol | Sodium phosphate dibasic | about 7.0 | 1 : 2.24 : 2.52 : 0.77 | 10.5% Dap 5% Sucrose 3% Mannitol 0.71% Na₂HPO₄ |

Fig. 7A

| ID No. | Lipopeptide [A] | Compound [B] | Compound [C] | Buffering Agent [D] | Compounding pH | Molar Ratio of existing components, respectively | Formulation in Solution upon addition of diluent (weight/volume) |
|---|---|---|---|---|---|---|---|
| 9 | daptomycin | Sucrose | Mannitol | Sodium phosphate dibasic | about 7.0 | 1 : 4.49 : 2.52 : 0.77 | 10.5% Dap<br>10% Sucrose<br>3% Mannitol<br>0.71% Na$_2$HPO$_4$ |
| 10 | daptomycin | Sucrose | Mannitol | Sodium phosphate dibasic | about 7.0 | 1 : 1.12 : 5.04 : 0.77 | 10.5% Dap<br>2.5% Sucrose<br>6% Mannitol<br>0.71% Na$_2$HPO$_4$ |
| 11 | daptomycin | Sucrose | Mannitol | Sodium phosphate dibasic | about 7.0 | 1 : 2.24 : 5.04 : 0.77 | 10.5% Dap<br>5% Sucrose<br>6% Mannitol<br>0.71% Na$_2$HPO$_4$ |
| 12 | daptomycin | Sucrose | Mannitol | Sodium phosphate dibasic | about 7.0 | 1 : 4.49 : 5.04 : 0.77 | 10.5% Dap<br>10% Sucrose<br>6% Mannitol<br>0.71% Na$_2$HPO$_4$ |
| 13 | daptomycin | Sucrose | | Sodium phosphate dibasic | about 7.0 | 1 : 8.98 : 0.77 | 10.5% Dap<br>20% Sucrose<br>0.71% Na$_2$HPO$_4$ |
| 14 | daptomycin | Trehalose | | Sodium phosphate dibasic | about 7.0 | 1 : 21.32 : 0.77 | 10.5% Dap<br>25% Trehalose<br>0.71% Na$_2$HPO$_4$ |
| 15 | daptomycin | Trehalose | | | about 4.7 | 1 : 21.32 | 10.5% Dap<br>25% Trehalose |
| 16 | daptomycin | Sucrose | | | about 4.7 | 1 : 1.12 | 10.5% Dap<br>2.5% Sucrose |
| 17 | daptomycin | Sucrose | | | about 4.7 | 1 : 2.24 | 10.5% Dap<br>5% Sucrose |
| 18 | daptomycin | Sucrose | | | about 4.7 | 1 : 4.49 | 10.5% Dap<br>10% Sucrose |
| 19 | daptomycin | Sucrose | | | about 4.7 | 1 : 8.98 | 10.5% Dap<br>20% Sucrose |

Fig. 7B

| ID No. | Lipopeptide [A] | Compound [B] | Compound [C] | Buffering Agent [D] | Compounding pH | Molar Ratio of existing components, respectively | Formulation in Solution upon addition of diluent (weight/volume) |
|---|---|---|---|---|---|---|---|
| 20 | daptomycin | Sucrose | Mannitol | | about 4.7 | 1 : 1.12 : 2.52 | 10.5% Dap<br>2.5% Sucrose<br>3% Mannitol |
| 21 | daptomycin | Sucrose | Mannitol | | about 4.7 | 1 : 2.24 : 2.52 | 10.5% Dap<br>5% Sucrose<br>3% Mannitol |
| 22 | daptomycin | Sucrose | Mannitol | | about 4.7 | 1 : 4.49 : 2.52 | 10.5% Dap<br>10% Sucrose<br>3% Mannitol |
| 23 | daptomycin | Sucrose | Mannitol | | about 4.7 | 1 : 6.73 : 2.52 | 10.5% Dap<br>15% Sucrose<br>3% Mannitol |
| 24 | daptomycin | Sucrose | Mannitol | | about 4.7 | 1 : 1.12 : 5.04 | 10.5% Dap<br>2.5% Sucrose<br>6% Mannitol |
| 25 | daptomycin | Sucrose | Mannitol | | about 4.7 | 1 : 2.24 : 5.04 | 10.5% Dap<br>5% Sucrose<br>6% Mannitol |
| 26 | daptomycin | Sucrose | Mannitol | | about 4.7 | 1 : 4.49 : 5.04 | 10.5% Dap<br>10% Sucrose<br>6% Mannitol |
| 27 | daptomycin | Sucrose | Mannitol | | about 4.7 | 1 : 6.73 : 5.04 | 10.5% Dap<br>15% Sucrose<br>6% Mannitol |
| 28 | daptomycin | Sucrose | Mannitol | Sodium phosphate dibasic | about 7.0 | 1 : 6.73 : 2.24 : 0.77 | 10.5% Dap<br>15% Sucrose<br>3% Mannitol<br>0.71% Na$_2$HPO$_4$ |
| 29 | daptomycin | Sucrose | Mannitol | Sodium phosphate dibasic | about 7.0 | 1 : 6.73 : 5.04 : 0.77 | 10.5% Dap<br>15% Sucrose<br>6% Mannitol<br>0.71% Na$_2$HPO$_4$ |

Fig. 7C

| ID No. | Lipopeptide [A] | Compound [B] | Compound [C] | Buffering Agent [D] | Compounding pH | Molar Ratio of existing components, respectively | Formulation in Solution upon addition of diluent (weight/volume) |
|---|---|---|---|---|---|---|---|
| 30 | daptomycin | Lactose | | Sodium phosphate dibasic | about 7.0 | 1 : 4.49 : 0.77 | 10.5% Dap<br>10% Lactose<br>0.71% Na₂HPO₄ |
| 31 | daptomycin | Maltose | | Sodium phosphate dibasic | about 7.0 | 1 : 4.49 : 0.77 | 10.5% Dap<br>10% Maltose<br>0.71% Na₂HPO₄ |
| 32 | daptomycin | Fructose | | Sodium phosphate dibasic | about 7.0 | 1 : 8.52 : 0.77 | 10.5% Dap<br>10% Fructose<br>0.71% Na₂HPO₄ |
| 33 | daptomycin | Dextrose | | Sodium phosphate dibasic | about 7.0 | 1 : 8.52 : 0.77 | 10.5% Dap<br>10% Dextrose<br>0.71% Na₂HPO₄ |
| 34 | daptomycin | Dextrose | Fructose | Sodium phosphate dibasic | about 7.0 | 1 : 4.26 : 4.26 : 0.77 | 10.5% Dap<br>5% Dextrose<br>5% Fructose<br>0.71% Na₂HPO₄ |
| 35 | daptomycin | Lactose | | Sodium phosphate dibasic | about 7.0 | 1 : 8.98 : 0.77 | 10.5% Dap<br>20% Lactose<br>0.71% Na₂HPO₄ |
| 36 | daptomycin | Maltose | | Sodium phosphate dibasic | about 7.0 | 1 : 8.98 : 0.77 | 10.5% Dap<br>20% Maltose<br>0.71% Na₂HPO₄ |
| 37 | daptomycin | Fructose | | Sodium phosphate dibasic | about 7.0 | 1 : 17.05 : 0.77 | 10.5% Dap<br>20% Fructose<br>0.71% Na₂HPO₄ |
| 38 | daptomycin | Dextrose | | Sodium phosphate dibasic | about 7.0 | 1 : 17.05 : 0.77 | 10.5% Dap<br>20% Dextrose<br>0.71% Na₂HPO₄ |
| 39 | daptomycin | Dextrose | Fructose | Sodium phosphate dibasic | about 7.0 | 1 : 8.52 : 8.52 : 0.77 | 10.5% Dap<br>10% Dextrose<br>10% Fructose<br>0.71% Na₂HPO₄ |

Fig. 7D

| ID No | Lipopeptide [A] | Compound [B] | Compound [C] | Buffering Agent [D] | Compounding pH | Molar Ratio of existing components, respectively | Formulation in Solution upon addition of diluent (weight/volume) |
|---|---|---|---|---|---|---|---|
| 40 | daptomycin | Lactose | | | about 4.7 | 1 : 4.49 | 10.5% Dap 10% Lactose |
| 41 | daptomycin | Maltose | | | about 4.7 | 1 : 4.49 | 10.5% Dap 10% Maltose |
| 42 | daptomycin | Fructose | | | about 4.7 | 1 : 8.52 | 10.5% Dap 10% Fructose |
| 43 | daptomycin | Dextrose | | | about 4.7 | 1 : 8.52 | 10.5% Dap 10% Dextrose |
| 44 | daptomycin | Dextrose | Fructose | | about 4.7 | 1 : 4.26 : 4.26 | 10.5% Dap 5% Dextrose 5% Fructose |
| 45 | daptomycin | Lactose | | | about 4.7 | 1 : 8.98 | 10.5% Dap 20% Lactose |
| 46 | daptomycin | Maltose | | | about 4.7 | 1 : 8.98 | 10.5% Dap 20% Maltose |
| 47 | daptomycin | Fructose | | | about 4.7 | 1 : 17.05 | 10.5% Dap 20% Fructose |
| 48 | daptomycin | Dextrose | | | about 4.7 | 1 : 17.05 | 10.5% Dap 20% Dextrose |
| 49 | daptomycin | Dextrose | Fructose | | about 4.7 | 1 : 8.52 : 8.52 | 10.5% Dap 10% Dextrose 10% Fructose |
| 50 | daptomycin | Lactose | | Sodium phosphate dibasic | about 7.0 | 1 : 1.12 : 0.77 | 10.5% Dap 2.5% Lactose 0.71% Na$_2$HPO$_4$ |
| 51 | daptomycin | Maltose | | Sodium phosphate dibasic | about 7.0 | 1 : 1.12 : 0.77 | 10.5% Dap 2.5% Maltose 0.71% Na$_2$HPO$_4$ |
| 52 | daptomycin | Fructose | | Sodium phosphate dibasic | about 7.0 | 1 : 2.13 : 0.77 | 10.5% Dap 2.5% Fructose 0.71% Na$_2$HPO$_4$ |

Fig. 7E

| ID No. | Lipopeptide [A] | Compound [B] | Compound [C] | Buffering Agent [D] | Compounding pH | Molar Ratio of existing components, respectively | Formulation in Solution upon addition of diluent (weight/volume) |
|---|---|---|---|---|---|---|---|
| 53 | daptomycin | Dextrose | | Sodium phosphate dibasic | about 7.0 | 1 : 2.13 : 0.77 | 10.5% Dap<br>2.5% Dextrose<br>0.71% Na₂HPO₄ |
| 54 | daptomycin | Dextrose | Fructose | Sodium phosphate dibasic | about 7.0 | 1 : 1.07 : 1.07 : 0.77 | 10.5% Dap<br>2.5% 1.25% Dextrose<br>1.25% Fructose<br>0.71% Na₂HPO₄ |
| 55 | daptomycin | Lactose | | Sodium phosphate dibasic | about 7.0 | 1 : 2.24 : 0.77 | 10.5% Dap<br>5% Lactose<br>0.71% Na₂HPO₄ |
| 56 | daptomycin | Maltose | | Sodium phosphate dibasic | about 7.0 | 1 : 2.24 : 0.77 | 10.5% Dap<br>5% Maltose<br>0.71% Na₂HPO₄ |
| 57 | daptomycin | Fructose | | Sodium phosphate dibasic | about 7.0 | 1 : 4.26 : 0.77 | 10.5% Dap<br>5% Fructose<br>0.71% Na₂HPO₄ |
| 58 | daptomycin | Dextrose | | Sodium phosphate dibasic | about 7.0 | 1 : 4.26 : 0.77 | 10.5% Dap<br>5% Dextrose<br>0.71% Na₂HPO₄ |
| 59 | daptomycin | Dextrose | Fructose | Sodium phosphate dibasic | about 7.0 | 1 : 2.13 : 2.13 : 0.77 | 10.5% Dap<br>2.5% Dextrose<br>2.5% Fructose<br>0.71% Na₂HPO₄ |
| 60 | daptomycin | Lactose | | | about 4.7 | 1 : 1.12 | 10.5% Dap<br>2.5% Lactose |
| 61 | daptomycin | Maltose | | | about 4.7 | 1 : 1.12 | 10.5% Dap<br>2.5% Maltose |
| 62 | daptomycin | Fructose | | | about 4.7 | 1 : 2.13 | 10.5% Dap<br>2.5% Fructose |
| 63 | daptomycin | Dextrose | | | about 4.7 | 1 : 2.13 | 10.5% Dap<br>2.5% Dextrose |
| 64 | daptomycin | Dextrose | Fructose | | about 4.7 | 1 : 1.07 : 1.07 : | 10.5% Dap<br>1.25% Dextrose<br>1.25% Fructose |

Fig. 7F

| ID No. | Lipopeptide [A] | Compound [B] | Compound [C] | Buffering Agent [D] | Compounding pH | Molar Ratio of existing components, respectively | Formulation in Solution upon addition of diluent (weight/volume) |
|---|---|---|---|---|---|---|---|
| 65 | daptomycin | Lactose | | | about 4.7 | 1 : 2.24 | 10.5% Dap<br>5% Lactose |
| 66 | daptomycin | Maltose | | | about 4.7 | 1 : 2.24 | 10.5% Dap<br>5% Maltose |
| 67 | daptomycin | Fructose | | | about 4.7 | 1 : 4.26 | 10.5% Dap<br>5% Fructose |
| 68 | daptomycin | Dextrose | | | about 4.7 | 1 : 4.26 | 10.5% Dap<br>5% Dextrose |
| 69 | daptomycin | Dextrose | Fructose | | about 4.7 | 1 : 2.13 : 2.13 | 10.5% Dap<br>2.5% Dextrose<br>2.5% Fructose |
| 70 | daptomycin | Mannitol | | | about 4.7 | 1 : 5.04 | 10.5% Dap<br>6% Mannitol |
| 71 | daptomycin | Mannitol | | Sodium phosphate dibasic | about 7.0 | 1 : 5.04 : 0.77 | 10.5% Dap<br>6% Mannitol<br>0.73% Na$_2$HPO$_4$ |
| 72 | daptomycin | Glycine | | | about 4.7 | 1 : 10.23 | 10.5% Dap<br>5% Glycine |
| 73 | daptomycin | Glycine | | Sodium phosphate dibasic | about 7.0 | 1 : 10.23 : 0.77 | 10.5% Dap<br>5% Glycine<br>0.73% Na$_2$HPO$_4$ |
| 74 | daptomycin | Sucrose | | | about 4.7 | 1 : 6.73 | 10.5% Dap<br>15% Sucrose |
| 75 | daptomycin | Sucrose | | Sodium phosphate dibasic | about 7.0 | 1 : 6.73 : 0.77 | 10.5% Dap<br>15% Sucrose<br>0.73% Na$_2$HPO$_4$ |
| 76 | daptomycin | Sucrose | | Sodium phosphate dibasic | about 4.7 | 1 : 6.73 : 0.77 | 10.5% Dap<br>15% Sucrose<br>0.73% Na$_2$HPO$_4$ |

Fig. 7G

| ID No. | Lipopeptide [A] | Compound [B] | Compound [C] | Buffering Agent [D] | Compounding pH | Molar Ratio of existing components, respectively | Formulation in Solution upon addition of diluent (weight/volume) |
|---|---|---|---|---|---|---|---|
| 77 | daptomycin | Trehalose | | | about 4.7 | 1 : 4.26 | 10.5% Dap 5% Trehalose |
| 78 | daptomycin | Trehalose | | | about 4.7 | 1 : 8.53 | 10.5% Dap 10% Trehalose |
| 79 | daptomycin | Trehalose | | | about 4.7 | 1 : 14.92 | 10.5% Dap 17.5% Trehalose |

Fig. 7H

Table 9

| Formulation ID | Formulation Description | Daptomycin Stability Ratio at 40 Degrees C | | | | | |
|---|---|---|---|---|---|---|---|
| | | T0 | 1 month | 2 months | 3 months | 6 months |
| 0 | Daptomycin Control with 50mM Phosphate buffer at pH 7.0 (without sugar or glycine) | 0.000 | 1.000 | 1.000 | 1.000 | 1.000 |
| 1 | 2.5% Trehalose, 50mM PO4, pH 7.0 | 0.000 | 0.667 | 0.800 | 0.667 | 1.000 |
| 2 | 5 % Trehalose, 50mM PO4, pH 7.0 | 0.000 | 0.867 | 0.867 | 0.714 | 0.871 |
| 3 | 10 % Trehalose, 50mM PO4, pH 7.0 | 0.000 | 0.400 | 0.400 | 0.381 | 0.613 |
| 4 | 2.5% Sucrose, 50mM PO4, pH 7.0 | 0.000 | 0.533 | 0.467 | 0.524 | 0.742 |
| 5 | 5% Sucrose, 50mM PO4, pH 7.0 | 0.000 | 0.467 | 0.533 | 0.476 | 0.645 |
| 6 | 10% Sucrose, 50mM PO4, pH 7.0 | 0.000 | 0.267 | 0.133 | 0.238 | 0.355 |
| 7 | 2.5% Sucrose, 3% Mannitol, 50mM PO4, pH 7.0 | 0.000 | 0.267 | 0.133 | 0.238 | 0.387 |
| 8 | 5 % Sucrose, 3% Mannitol, 50mM PO4, pH 7.0 | 0.000 | 0.267 | 0.133 | 0.190 | 0.258 |
| 9 | 10 % Sucrose, 3% Mannitol, 50mM PO4, pH 7.0 | 0.000 | -0.200 | 0.267 | 0.190 | 0.226 |
| 10 | 2.5% Sucrose, 6% Mannitol, 50mM PO4, pH 7.0 | 0.000 | -0.067 | 0.333 | 0.238 | 0.355 |
| 11 | 5% Sucrose, 6% Mannitol, 50mM PO4, pH 7.0 | 0.000 | -0.200 | 0.133 | 0.238 | 0.290 |
| 12 | 10% Sucrose, 6% Mannitol, 50mM PO4, pH 7.0 | 0.000 | 0.000 | 0.067 | 0.143 | 0.419 |
| 13 | 20 % Sucrose, 50mM PO4, pH 7.0 | 0.000 | -0.267 | 0.133 | 0.381 | 0.226 |
| 14 | 25% Trehalose, 50mM PO4, pH 7.0 | 0.000 | 0.133 | 0.533 | 0.381 | 0.484 |
| 15 | 25% Trehalose, pH 4.7 | 0.000 | -0.067 | NT | 0.286 | 0.323 |
| 16 | 2.5% Sucrose, PO4, pH 4.7 | 0.000 | 0.333 | 0.600 | 0.429 | 0.581 |
| 17 | 5% Sucrose, PO4, pH 4.7 | 0.000 | 0.133 | 0.267 | 0.190 | 0.323 |
| 18 | 10 % Sucrose, PO4, pH 4.7 | 0.000 | 0.067 | 0.133 | 0.095 | 0.194 |
| 19 | 20% Sucrose, PO4, pH 4.7 | 0.000 | -0.467 | -0.067 | 0.000 | 0.097 |
| 20 | 2.5% Sucrose, 3% Mannitol, pH 4.7 | 0.000 | 0.000 | 0.200 | 0.429 | 0.484 |
| 21 | 5% Sucrose, 3% Mannitol, pH 4.7 | 0.000 | 0.000 | 0.133 | 0.333 | 0.387 |
| 22 | 10 % Sucrose, 3% Mannitol, pH 4.7 | 0.000 | 0.333 | 0.200 | 0.381 | 0.226 |

Fig. 8A

| Formulation ID | Formulation Description | Daptomycin Stability Ratio at 40 Degrees C. | | | | |
|---|---|---|---|---|---|---|
| | | T0 | 1 month | 2 months | 3 months | 6 months |
| 23 | 15 % Sucrose, 3% Mannitol, pH 4.7 | 0.000 | 0.133 | 0.000 | 0.190 | 0.129 |
| 24 | 2.5% Sucrose, 6% Mannitol, pH 4.7 | 0.000 | 0.400 | 0.400 | 0.571 | 0.516 |
| 25 | 5% Sucrose, 6% Mannitol, pH 4.7 | 0.000 | 0.333 | 0.333 | 0.476 | 0.419 |
| 26 | 10% Sucrose, 6% Mannitol, pH 4.7 | 0.000 | 0.200 | 0.067 | 0.238 | 0.226 |
| 27 | 15% Sucrose, 6% Mannitol, pH 4.7 | 0.000 | 0.200 | 0.067 | 0.286 | 0.226 |
| 35 | 20%Lactose with 50mM Phosphate buffer at pH 7.0 | 0.000 | 2.600 | 0.800 | 0.524 | 0.484 |
| 45 | 20% Lactose at pH 4.7 | 0.000 | 2.267 | 2.867 | 1.571 | 2.161 |
| 50 | 2.5%Lactose with 50mM Phosphate buffer at pH 7.0 | 0.000 | 2.667 | 4.733 | 3.286 | 2.935 |
| 51 | 2.5%Maltose with 50mM Phosphate buffer at pH 7.0 | 0.000 | 2.933 | 4.467 | 3.476 | 3.129 |
| 52 | 2.5% Fructose with 50mM Phosphate buffer at pH 7.0 | 0.000 | 3.133 | 4.800 | 3.905 | 4.032 |
| 53 | 2.5%Dextrose with 50mM Phosphate buffer at pH 7.0 | 0.000 | 7.467 | 12.400 | 9.333 | 8.516 |
| 54 | 2.5% Dextrose/Fructose (1:1) with 50mM Phosphate buffer at pH 7.0 | 0.000 | 5.400 | 8.267 | 6.857 | 6.419 |
| 55 | 5.0% Lactose with 50mM Phosphate buffer at pH 7.0 | 0.000 | 3.067 | 4.800 | 3.810 | 3.419 |
| 56 | 5.0% Maltose with 50mM Phosphate buffer at pH 7.0 | 0.000 | 3.400 | 4.800 | 4.048 | 3.355 |
| 57 | 5.0%Fructose with 50mM Phosphate buffer at pH 7.0 | 0.000 | 2.533 | 4.133 | 3.190 | 3.355 |
| 58 | 5.0%Dextrose with 50mM Phosphate buffer at pH 7.0 | 0.000 | 7.667 | 11.133 | 8.905 | 8.258 |
| 59 | 5.0% Dextrose/Fructose (1:1) with 50mM Phosphate buffer at pH 7.0 | 0.000 | 4.267 | 7.600 | 6.524 | 6.161 |
| 60 | 2.5% Lactose pH 4.7 | 0.000 | 2.267 | 3.533 | 2.905 | 2.774 |
| 61 | 2.5% Maltose pH 4.7 | 0.000 | 2.133 | 3.600 | 2.905 | 2.645 |
| 62 | 2.5% Fructose pH 4.7 | 0.000 | 3.133 | 4.933 | 3.905 | 3.968 |
| 63 | 2.5%Dextrose pH 4.7 | 0.000 | 9.267 | 14.400 | 10.952 | 9.903 |
| 64 | 2.5%Dextrose/Fructose(1:1) pH 4.7 | 0.000 | 5.000 | 9.267 | 7.571 | 7.645 |

Fig. 8B

| Formulation ID | Formulation Description | Daptomycin Stability Ratio at 40 Degrees C | | | | |
|---|---|---|---|---|---|---|
| | | T0 | 1 month | 2 months | 3 months | 6 months |
| 65 | 5.0% Lactose pH 4.7 | 0.000 | 2.333 | 3.333 | 2.571 | 2.452 |
| 66 | 5.0% Maltose pH 4.7 | 0.000 | 2.133 | 3.600 | 2.905 | 2.645 |
| 67 | 5.0% Fructose pH 4.7 | 0.000 | 2.200 | 4.467 | 3.810 | 3.581 |
| 68 | 5.0% Dextrose pH 4.7 | 0.000 | 4.200 | 8.867 | 7.000 | 7.516 |
| 69 | 5.0% Dextrose/Fructose (1:1) pH 4.7 | 0.000 | 3.333 | 7.200 | 6.048 | 6.452 |
| 70 | 6% Mannitol, pH 4.7 | 0.000 | 0.533 | 0.867 | 0.667 | 0.903 |
| 71 | 6% Mannitol, 50 mM PO4, pH 7.0 | 0.000 | 0.533 | 0.600 | 0.524 | 0.645 |
| 72 | 5% Glycine, pH 4.7 | 0.000 | 0.600 | 1.000 | 0.667 | 0.935 |
| 73 | 5% Glycine, 50 mM PO4, pH 7.0 | 0.000 | 1.267 | 1.867 | 1.524 | 1.742 |
| 74 | 15% Sucrose, PO4, pH 4.7 | 0.000 | 0.000 | 0.200 | -0.095 | 0.161 |
| 75 | 15% Sucrose, 50mM PO4, pH 7.0 | 0.000 | 0.000 | 0.200 | 0.286 | 0.065 |
| 76 | 15% Sucrose, 50mM PO4, pH 7.0 | 0.000 | 0.067 | 0.267 | 0.048 | 0.226 |
| 77 | 5 % Trehalose, pH 4.7 | 0.000 | 0.487 | NT | 0.595 | 0.639 |
| 78 | 10 % Trehalose, pH 4.7 | 0.000 | 0.420 | NT | 0.490 | 0.458 |
| 79 | 17.5% Trehalose, pH 4.7 | 0.000 | 0.293 | NT | 0.257 | 0.313 |

Fig. 8C

LIPOPEPTIDE COMPOSITIONS AND RELATED METHODS

RELATED APPLICATIONS

This application is a divisional of U.S. application Ser. No. 13/511,246, filed May 22, 2012, which is a national stage application of PCT Application No. PCT/US2010/057910, filed Nov. 23, 2010, which claims the benefit of U.S. provisional patent application 61/263,784, filed on Nov. 23, 2009, the entire contents of which are incorporated herein by reference.

TECHNICAL FIELD

The present invention relates to improved lipopeptide compositions for reconstitution in a liquid diluent to form a pharmaceutical composition for parenteral administration, as well as methods of making the solid lipopeptide compositions. Preferred improved lipopeptide compositions include solid daptomycin preparations with increased rates of reconstitution in aqueous liquids and/or increased daptomycin chemical stability.

BACKGROUND

Daptomycin is a cyclic lipopeptide antibiotic indicated for the treatment of complicated skin and skin structure infections and bacteremia, including bacteremia with suspected or proven infective endocarditis. Daptomycin for injection can be administered intravenously to treat indicated infections caused by susceptible strains of multiple Gram-positive microorganisms including methicillin-resistant *Staphylococcus aureus* (MRSA). Daptomycin for injection (CUBICIN®, Cubist Pharmaceuticals, Inc., Lexington, Mass.) is supplied as a lyophilized powder that is reconstituted and compounded as a pharmaceutical composition for parenteral administration. The reconstituted daptomycin composition can be compounded as a pharmaceutical composition for parenteral administration, for example by combination with a medically appropriate amount of pharmaceutical diluent (e.g., 0.9% aqueous sodium chloride). The diluent can be the same or different. The parenteral pharmaceutical composition including daptomycin can be administered by intravenous infusion. The lyophilized powder containing daptomycin can take 15-45 minutes to reconstitute in a pharmaceutical diluent, depending on the reconstitution procedure.

Daptomycin (FIG. 1) can be derived from the fermentation product of the microorganism *Streptomyces roseosporus* with a feed of n-decanoic acid. Baltz in *Biotechnology of Antibiotics*. 2nd Ed., ed. W. R. Strohl (New York: Marcel Dekker, Inc.), 1997, pp. 415-435. Initial attempts to separate daptomycin from structurally similar components in the fermentation product lead to the identification of other structurally similar compounds including anhydro-daptomycin (FIG. 2), beta-isomer of daptomycin (FIG. 3) and a lactone hydrolysis product of daptomycin (FIG. 4). Anhydro-daptomycin (FIG. 2) can be formed while performing techniques to separate daptomycin from structurally similar components in the fermentation product. Rehydration of the anhydro-succinimido form produces a second degradation product that contains a β-aspartyl group and is designated the β-isomer form of daptomycin (FIG. 3). Kirsch et al. (Pharmaceutical Research, 6:387-393, 1989, "Kirsch") disclose anhydro-daptomycin and the beta-isomer of daptomycin produced in the purification of daptomycin. Kirsch described methods to minimize the levels of anhydro-daptomycin and the β-isomer through manipulation of pH conditions and temperature conditions. However, Kirsch was unable to stabilize daptomycin and prevent the conversion of daptomycin to anhydro-daptomycin and its subsequent isomerization to β-isomer. Kirsch was also unable to prevent the degradation of daptomycin into other degradation products unrelated to anhydro-daptomycin and β-isomer.

U.S. Pat. No. 6,696,412 discloses several additional compounds present in the fermentation product from which daptomycin is derived, and provides methods for purifying daptomycin with increased purity. The additional compounds include the lactone hydrolysis product of daptomycin, having the chemical structure of FIG. 4. The daptomycin purification methods can include forming daptomycin micelles, removing low molecular weight contaminants by filtration, and then converting the daptomycin-containing micelle filtrate to a non-micelle state followed by anion exchange and reverse osmosis diafiltration to obtain the high-purity daptomycin that can then be lyophilized.

One measure of the chemical stability of daptomycin in the lyophilized daptomycin powder is the amount of daptomycin (FIG. 1) present in the reconstituted daptomycin composition relative to the amount of structurally similar compounds including anhydro-daptomycin (FIG. 2), beta-isomer of daptomycin (FIG. 3) and a lactone hydrolysis product of daptomycin (FIG. 4). The amount of daptomycin relative to the amount of these structurally similar compounds can be measured by high performance liquid chromatography (HPLC) after reconstitution in an aqueous diluent. The purity of daptomycin and amounts of structurally similar compounds (e.g., FIGS. 2-4) can be determined from peak areas obtained from HPLC (e.g., according to Example 4 herein) to provide a measure of daptomycin chemical stability in a solid form. The daptomycin purity and chemical stability can also be measured within the liquid reconstituted daptomycin composition over time as a measure of the reconstituted daptomycin chemical stability in a liquid form.

There is a need for solid lipopeptide compositions that rapidly reconstitute (e.g., in less than about 5 minutes) in a pharmaceutical diluent to form reconstituted lipopeptide compositions that can be compounded as pharmaceutical compositions. For example, to reconstitute a 500 mg vial of lyophilized daptomycin for injection (CUBICIN®), the lyophilized powder is combined with 10 mL of 0.9% aqueous sodium chloride, allowed to stand for 10 minutes (or more) and then gently rotated or swirled "a few minutes" to form the reconstituted daptomycin composition prior to formation to prepare a parenteral daptomycin pharmaceutical composition.

There is also a need for solid daptomycin compositions with improved chemical stability in the solid and/or reconstituted form (i.e., higher total percent daptomycin purity over time), providing advantages of longer shelf life, increased tolerance for more varied storage conditions (e.g., higher temperature or humidity) and increased chemical stability after reconstitution as a liquid formulation for parenteral administration.

SUMMARY

The present invention relates to solid lipopeptide compositions for reconstitution in aqueous diluent to form pharmaceutical compositions. The lipopeptide compositions are prepared by converting a pharmaceutically acceptable aqueous solution including the lipopeptide into the solid lipopeptide composition (e.g., by lyophilization, spray drying or the like).

The solid lipopeptide composition can be subsequently reconstituted in an aqueous pharmaceutically acceptable diluent to form a pharmaceutical product for parenteral administration.

In a first embodiment, the time for reconstituting the solid lipopeptide compositions in the aqueous diluent can be unexpectedly reduced by increasing the pH of the aqueous lipopeptide solution (preferably to a pH of about 6.5-7.5, most preferably about 7.0) prior to lyophilizing the solution to form the solid lipopeptide composition. For example, solid daptomycin compositions prepared by lyophilizing liquid daptomycin solutions (without a sugar or glycine) at a pH of about 7.0 reconstituted more rapidly in 0.9% aqueous sodium chloride than otherwise comparable daptomycin formulations lyophilized at a pH of about 4.7.

The reconstitution rate of certain solid lipopeptide compositions in aqueous diluent was also accelerated by combining the lipopeptide with glycine or a sugar (preferably, a non-reducing sugar) prior to converting the solution to the solid lipopeptide. For example, 500 mg of the lyophilized pharmaceutical daptomycin compositions in Table 6 formed from solutions including daptomycin and a non-reducing sugar or glycine at a pH of about 7.0 reconstituted in 0.9% aqueous sodium chloride in less than 2 minutes, with most compositions reconstituting in less than 1 minute.

The solid pharmaceutical lipopeptide preparations can be a product obtained by the following process: (a) forming an aqueous solution of the lipopeptide at a pH above the isoelectric point of the lipopeptide (e.g., above about 3.8 for daptomycin); (b) dissolving glycine or a sugar (preferably a non-reducing sugar) in the aqueous solution with the lipopeptide to form a liquid lipopeptide formulation; (c) adjusting the pH of the liquid lipopeptide formulation to about 6.5 to 7.5; and (d) converting the liquid lipopeptide formulation to the solid pharmaceutical lipopeptide composition (e.g., lyophilization). For example, a lyophilized daptomycin medicament preparation that reconstitutes in less than about 2 minutes in an aqueous 0.9% aqueous sodium chloride diluent can be prepared by: (a) forming an aqueous solution of daptomycin at a pH of about 4.5-5.0 (e.g., a pH of about 4.7); (b) adding a buffering agent including phosphate, citrate, maleate or a combination thereof to the aqueous solution of daptomycin to form a buffered daptomycin formulation; (c) dissolving one or more sugars in the buffered daptomycin formulation to form a buffered daptomycin sugar formulation containing about 2.5% w/v to about 25% w/v of the sugar(s) (e.g., about 3%, 4%, 5%, 6%, 7%, 8%, 9%, 10%, 11%, 12%, 13%, 14%, 15%, 16%, 17%, 18%, 19%, 20%, 21%, 22%, 23%, or 24%), the sugar(s) being selected from the group consisting of trehalose, sucrose, mannitol, and combinations thereof; (d) adjusting the pH of the buffered daptomycin sugar formulation to a pH of about 6.5 to 7.5 (e.g., 7.0); and (e) lyophilizing the buffered daptomycin sugar formulation to form the solid pharmaceutical daptomycin composition. Preferably, the sugar(s) include sucrose, sucrose and mannitol, or trehalose.

In a second embodiment, the present invention provides daptomycin compositions with improved daptomycin chemical stability, measured as higher total percent daptomycin purity over time (as determined by HPLC according to the method of Example 4). Surprisingly, the daptomycin contained in solid preparations with certain preferred compositions (e.g., daptomycin combined with sucrose or trehalose) was more chemically stable than daptomycin in daptomycin solid preparations without sugar or glycine. The chemical stability of daptomycin in a solid form was measured by comparing total daptomycin purity measurements from multiple solid daptomycin preparations each obtained according to Example 4. Higher chemical stability was measured as higher comparative daptomycin total purity measurements between two samples according to Example 4. For example, the chemical stability of daptomycin measured from solid daptomycin compositions containing one or more non-reducing sugars such as sucrose was unexpectedly increased by between 10% and greater than 90% during a 6-month storage period prior to reconstitution in 0.9% aqueous sodium chloride (compared to daptomycin chemical stability measured from solid daptomycin compositions without any sugar).

Also surprisingly, higher daptomycin chemical stability was observed for up to 14 days in reconstituted liquid daptomycin solutions at various temperatures in daptomycin preparations containing one or more certain non-reducing sugars (e.g., sucrose) than for comparable daptomycin formulations without sugar or glycine. For example, the chemical stability of the daptomycin in the reconstituted solution over 14 days was also unexpectedly increased for compositions containing daptomycin with certain non-reducing sugars (e.g., sucrose).

Preferred examples of solid pharmaceutical daptomycin preparations include about 2.5% to 25.0% of one or more non-reducing sugars or glycine. Other preferred examples of solid pharmaceutical daptomycin preparations including about 2.5% to 25.0% of a sugar selected from the group consisting of sucrose, mannitol, and trehalose. Particularly preferred solid pharmaceutical daptomycin preparations consist essentially of daptomycin, sucrose, a sodium phosphate buffering agent (e.g., Sodium phosphate dibasic, $Na_2HPO_4$) and up to about 8% of other materials (e.g., as measured by HPLC peak area at 214 nm according to Example 4).

Solid pharmaceutical daptomycin preparations can be obtained by converting an aqueous solution including daptomycin and a non-reducing sugar (e.g., 15-20% sucrose w/v in the solution) at a pH above the isoelectric point of daptomycin (e.g., a pH of about 3.7 or greater). Preferably, the pH of the aqueous solution containing daptomycin and a non-reducing sugar (e.g., sucrose) is about 4.5-8.0 (including, e.g., pH values of 4.5-7.5, 4.7-7.5, 5.0-7.5, 5.5-7.5, 4.7-7.0, 5.0-7.0, 5.5-7.0, 6.0-7.0, and 6.5-7.0 and values therebetween) when converted to the solid pharmaceutical daptomycin preparation (e.g., a powder). Preferably, a lyophilized daptomycin medicament preparation having a reconstitution time of about 2 minutes or less in an aqueous diluent is prepared by: (a) forming an aqueous solution of daptomycin at a pH of about 4.7-5.0; (b) adding a buffering agent including phosphate, citrate, TRIS, maleate or a combination thereof to the aqueous solution of daptomycin; (c) dissolving a sugar (e.g., a non-reducing sugar such as sucrose) in the aqueous solution with daptomycin to form a buffered daptomycin sugar formulation; (d) adjusting the pH of the buffered daptomycin sugar formulation to about 6.5 to 8.0 (including, e.g., pH values of 6.5-7.5, 6.5-7.0, 6.5, 7.0. 7.5, 8.0, 7.0-8.0, 7.0-7.5 and values therebetween); and (e) lyophilizing the buffered daptomycin sugar formulation to form the solid pharmaceutical daptomycin preparation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 5A-5E show Table 6, which lists examples of preferred daptomycin compositions. These compositions were prepared as liquid solutions, then lyophilized to provide solid pharmaceutical daptomycin preparations that reconstitute in an aqueous pharmaceutical diluent within less than 2 minutes (including compositions that reconstitute in less than 1 minute). In Table 6, "Recon time" refers to the time required for about 500 mg the lyophilized daptomycin composition described in the "Formulation (solid state)" column to dissolve in 10 mL of 0.9% aqueous sodium chloride at room temperature (about 25 degrees C.).

FIGS. 6A and 6B show Table 7, which lists examples of other daptomycin compositions. These compositions were prepared as liquid solutions, then lyophilized to provide solid pharmaceutical lipopeptide preparations that reconstitute in an aqueous pharmaceutical diluent within 2 minutes or more. In Table 7, "Recon time" refers to the time required for about 500 mg the lyophilized daptomycin solution to dissolve in 10 mL of 0.9% aqueous sodium chloride at room temperature (about 25 degrees C.).

FIGS. 7A-7H show Table 8, which lists examples of daptomycin compositions containing a sugar.

FIGS. 8A-8C show Table 9, which shows the percent change in total daptomycin purity measured and calculated for various daptomycin formulations according to Example 4.

DETAILED DESCRIPTION

Lipopeptide Compositions with Accelerated Reconstitution

In a first embodiment of the invention, solid pharmaceutical lipopeptide preparations are provided that have a reconstitution time less than 5 minutes in an aqueous pharmaceutical diluent. For example, 500 mg of a solid daptomycin pharmaceutical lipopeptide preparations prepared by lyophilization of a daptomycin solution including glycine or sugar(s) can be dissolved in 10 mL of 0.9% aqueous sodium chloride at room temperature (about 25 degrees C.) in 4 minutes or less (including dissolution times of 4, 3, 2, 1 and less than 1 minute).

Unexpectedly, certain solid pharmaceutical lipopeptide preparations obtained from a liquid lipopeptide formulation at a pH of about 7.0 reconstituted in an aqueous pharmaceutical diluent at a faster rate than otherwise identical solid pharmaceutical lipopeptide preparations obtained from a comparable liquid lipopeptide formulation at a lower pH (e.g., 4.7). For example, two aqueous solutions of daptomycin with identical compositions (without a sugar or glycine) at pH values of 4.7 and 7.0 upon lyophilization formed powders that reconstituted in 0.9% aqueous sodium chloride diluent in 5.0 minutes (for pH 4.7) compared to 1.4 minutes (for pH 7.0) (See Table 6 and Table 7). Furthermore, adding glycine or sugars (preferably, one or more non-reducing sugars) to the daptomycin formulation also increased the rate of reconstitution of the resulting solid pharmaceutical lipopeptide preparation.

Figure 1:
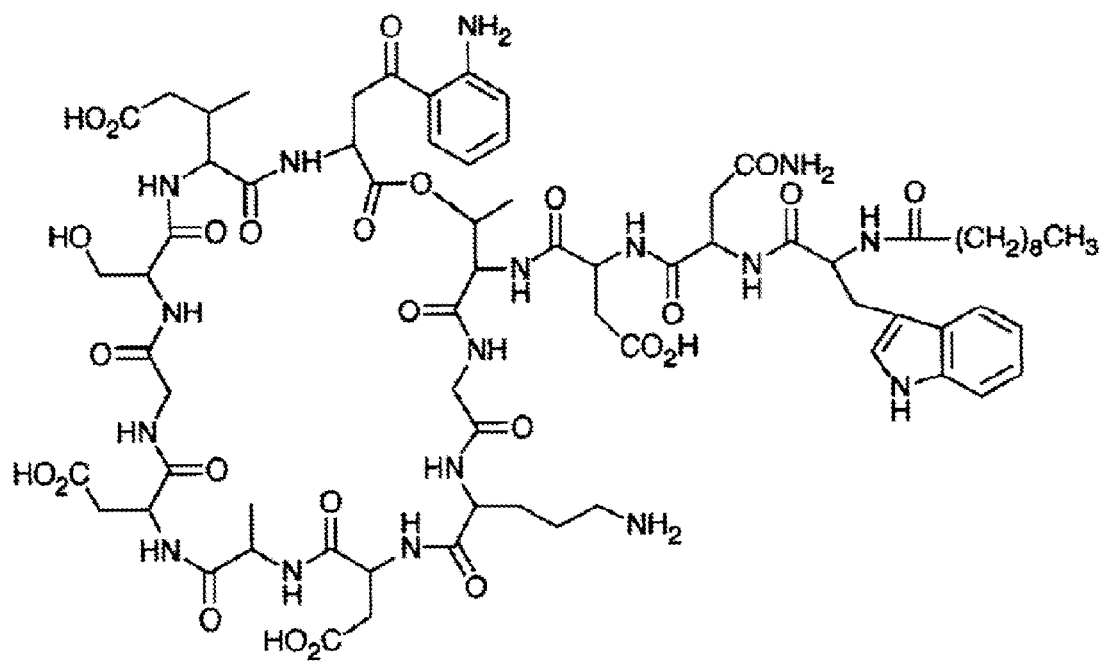
FIG. 1 is the chemical structure of daptomycin.

Solid pharmaceutical lipopeptide preparations having an accelerated reconstitution rate are obtainable from an aqueous solution of the lipopeptide at a suitable pH (e.g., 4.7-7.0) and temperature (e.g., 2-10 degrees C.). In general, the solid pharmaceutical lipopeptide preparations can be made from an aqueous solution of the lipopeptide at a pH above the isoelectric point of the lipopeptide. Preferably, the lipopeptide includes daptomycin (FIG. 1). Preferred methods for preparing solid pharmaceutical daptomycin preparations are described in Example 2a and 2b. Solid pharmaceutical daptomycin preparations can be prepared from an aqueous solution of daptomycin at a pH above the isoelectric point of daptomycin (e.g., a pH above about 3.7 or 3.8, including pH values of 4.5, 4.7, and other higher pH values disclosed herein) and at a temperature of 2-10 degrees C. The daptomycin can be obtained in a frozen solution in sterile water for injection (sWFI) at a concentration of 125-130 mg/mL, at pH 3.0 and subsequently pH adjusted to the desired pH by adding sodium hydroxide (e.g., 3.0-10.0 N, including 3.0 N and 10.0 N) at a temperature of about 2-10 degrees C. The pH can be adjusted, for example, by adding sodium hydroxide, hydrochloric acid, phosphoric acid and/or acetic acid.

A buffering agent is optionally added to the aqueous lipopeptide solutions above a pH of about 4.7. Buffering agents can include, for example, agents including phosphate, citrate, maleate, or carbonate moieties, or a combinations thereof, and pharmaceutically appropriate counterions. The amount of the buffering agent can be selected based on the molar ratio of the buffering agent to the daptomycin (e.g., as described in Table 6). The buffering agent can be added in anhydrous or aqueous form. Specific examples of buffering agents are a sodium or potassium salt of phosphoric acid, a sodium or potassium salt of boric acid, a sodium or potassium salt of citric acid, a sodium or potassium salt of carbonic acid, sodium phosphate (e.g., Sodium phosphate dibasic), TRIS (tris(hydroxymethyl)aminomethane and salt of maleic acid. In one aspect the buffering agent is selected from sodium phosphate dibasic ($Na_2HPO_4$), sodium citrate, sodium bicarbonate, histidine monohydrochloride TRIS and maleate. For aqueous daptomycin solutions, the buffer preferably includes about 50 mM of a phosphate buffering agent (e.g., sodium phosphate dibasic) added to the aqueous daptomycin solution at a pH of about 4.5-6.0 (preferably at a pH of about 5.0). The pH of an acidic aqueous lipopeptide solution (e.g., pH about 3.0) can be raised prior to adding the buffering agent by adding 3N sodium hydroxide under chilled conditions (2-10° C.) prior to adding the buffering agent(s).

One or more sugars (e.g., non-reducing sugars) and/or glycine can be added to the aqueous lipopeptide solution prior to converting the solution to the pharmaceutical lipopeptide preparations (e.g., by lyophilization). The amount and manner of combination of the glycine or sugar(s) with the aqueous lipopeptide solution is preferably selected to provide a liquid lipopeptide solution that can be subsequently adjusted to a pH of about 6.5 to 7.5 (e.g., by adding 3N sodium hydroxide at about 2-10 degrees C.). For a liquid daptomycin formulation, the glycine and/or one or more sugars is preferably combined by stirring at a suitable temperature (e.g., 2-10 degrees C.). The sugar(s) are preferably non-reducing sugars, although the aqueous daptomycin solutions can be prepared with glycine, trehalose, sucrose, mannitol, lactose, maltose, fructose, dextrose, and combinations thereof at a pH of about 5.0 or higher.

The molar ratio of the lipopeptide to the total amount of glycine and/or one or more sugars can be selected to obtain solid compositions with more rapid reconstitution rates in aqueous solvents (such as, e.g., compositions described in Table 6). For example, liquid daptomycin sugar solutions preferably include daptomycin and sucrose in a daptomycin: sucrose molar ratio of from [1.00:1.12] to about [1.00:8.98].

Figure 3:
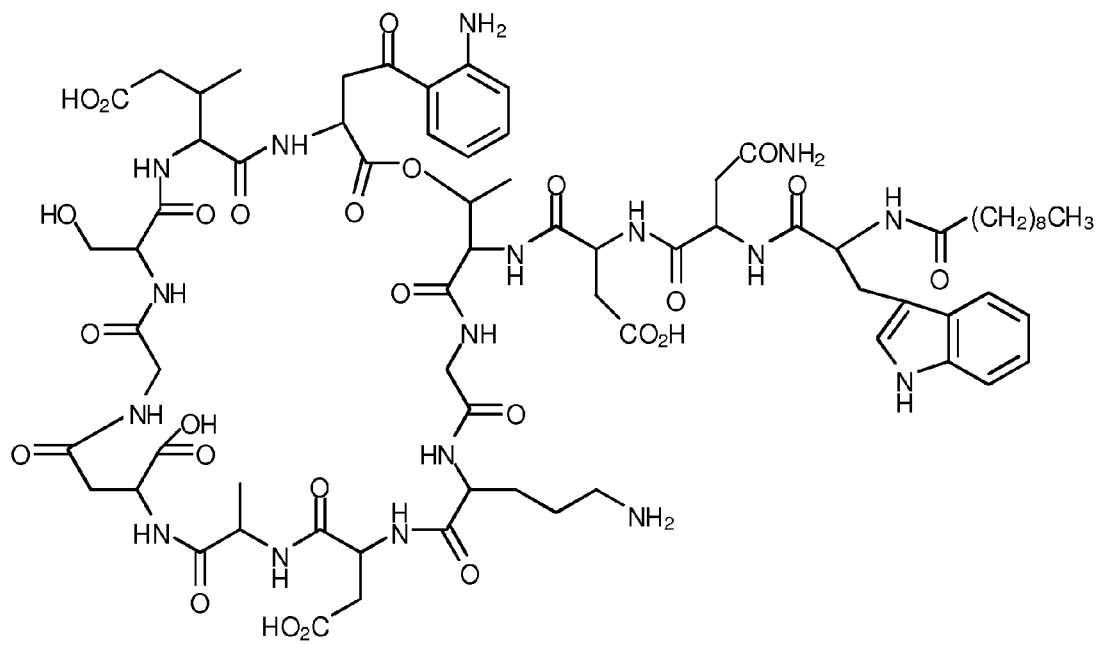
FIG. 3 is the chemical structure of the beta-isomer of daptomycin.

The pH of the lipopeptide solution can be adjusted to about 6.5-7.5 after combination of the lipopeptide, sugar(s) or glycine, and buffering agent(s), but prior to converting the liquid lipopeptide solution to the solid pharmaceutical preparation. Preferably, the lipopeptide includes daptomycin, and the liquid daptomycin formulation is adjusted to a pH of about 6.5-7.0 and most preferably to a pH of about 7.0 prior to conversion to a solid form, but after addition of the buffering agent(s) and the glycine and/or sugar(s). FIG. 5 (Table 6) describes examples of preferred liquid daptomycin compositions that were lyophilized to provide solid pharmaceutical lipopeptide preparations that rapidly reconstitute (dissolve) in an aqueous diluent For each of the compositions containing glycine and a non-reducing sugar in Table 6, 500 mg of the solid daptomycin sugar composition dissolved in 0.9% aqueous sodium chloride in less than 1 minute. In contrast, many of the solid pharmaceutical preparations described in Table 7 (FIG. 3) obtained from liquid daptomycin compositions at a pH of about 4.7 had longer reconstitution times than compositions in Table 6 (e.g., 500 mg of the solid pharmaceutical daptomycin compositions described in Table 7 took 2 minutes or more to reconstitute in 10 mL of 0.9% aqueous sodium chloride diluent at 25 degrees C.).

The liquid lipopeptide formulation can be converted to the solid pharmaceutical lipopeptide composition by any suitable method, including lyophilization, spray-drying or fluid bed drying. Example 3 describes the lyophilization methods used to convert certain liquid daptomycin formulations in Table 6 to solid pharmaceutical daptomycin preparations prior to measuring the reconstitution times also provided in Table 6. The solid daptomycin compositions can be a lyophilized, freeze-dried, spray-dried, fluid-bed dried, spray congealed, precipitated or crystallized powder or amorphous solid. In one aspect the powder is a lyophilized or spray-dried powder. In another aspect of the invention, the powder is a lyophilized powder.

The molar ratio of daptomycin to the sugar in a solid pharmaceutical daptomycin preparation is preferably in the range of about [1:1.12] to about [1:21.32]. For example, a solid pharmaceutical daptomycin preparation can include sucrose with a molar ratio of daptomycin to sucrose of about [1:1.12] to about [1:8.98], including daptomycin:sucrose molar ratios of [1:4.49] to [1:8.98], [1:6.73] to [1:8.98], [1:1.12], [1:1.344], [1:1.792], [1:2.24], [1:2.688], [1:3.136], [1:3.584], [1:4.032], [1:4.49], [1:4.928], [1:5.376], [1:5.824], [1:6.272], [1:6.73], [1:7.168], [1:7.616], [1:8.064], [1:8.512], or [1:8.98]. In one aspect the excipient is mannitol and the molar ratio of daptomycin to mannitol is about [1:2.52] to about [1:5.04]. In another aspect the molar ratio of daptomycin to mannitol is [1:2.52], [1:3.36], [1:4.20] or [1:5.04]. In another aspect the excipient is sucrose and the molar ratio of daptomycin to sucrose is about [1:1.12] to about [1:8.98]. In another aspect the molar ratio of daptomycin to sucrose is [1:4.49] to about [1:8.98]. In another aspect the molar ratio of daptomycin to sucrose is about [1:6.73] to about [1:8.98]. In another aspect the molar ratio of daptomycin to sucrose is [1:1.12], [1:1.344], [1:1.792], [1:2.24], [1:2.688], [1:3.136], [1:3.584], [1:4.032], [1:4.49], [1:4.928], [1:5.376], [1:5.824], [1:6.272], [1:6.73], [1:7.168], [1:7.616], [1:8.064], [1:8.512], or [1:8.98]. In another aspect the excipient is trehalose and the daptomycin to trehalose molar ratio is [1:2.13] to about [1:21.32]. In another aspect, the molar ratio of daptomycin to trehalose is [1:2.13], [1:2.556], [1:3.408], [1:4.26], [1:5.112], [1:5.964], [1:6.816], [1:7.668], [1:8.53], [1:9.372], [1:10.224], [1:11.076], [1:11.928], [1:12.78], [1:13.632], [1:14.484], [1:14.91], [1:15.336], [1:16.188], [1:17.04], [1:17.892], [1:18.744], [1:19.592], [1:20.448], or [1:21.32].

The solid pharmaceutical lipopeptide composition can be reconstituted and combined with one or more pharmaceutically acceptable diluents to obtain a pharmaceutical composition for parenteral administration. The ratio of the daptomycin in the reconstituted liquid composition to diluent is preferably between 25 mg/mL to 200 mg/mL. For example, a lyophilized composition including daptomycin can be reconstituted in a vial by adding 0.9% aqueous sodium chloride to the lyophilized composition. The reconstituted daptomycin solution can be combined with medically appropriate diluent and administered intravenously. Pharmaceutically-acceptable diluent include sterile Water for Injection (sWFI), 0.9% sterile sodium chloride injection (sSCl), bacteriostatic water for injection (bWFI), and Ringer's solution. Additional examples of suitable diluent can be found in *Remington's Pharmaceutical Sciences*, 17$^{th}$ Ed., A. R Gennaro, Ed., Mack Publishing Co., Easton, Pa. 1985. The diluent can be sterile Water for Injection or sterile sodium chloride injection. Preferred diluent are sWFI or lactated Ringers injection. Preferably, the diluent is not added slowly while rotating at a 45 degree angle. Also preferably, after addition of the diluent, the vessel containing the daptomycin is not allowed to sit undisturbed for 10 minutes prior to agitation.

Optionally, the diluent further includes a pharmaceutically-acceptable preservative. In one aspect the preservative is benzyl alcohol, chlorobutanol, m-cresol, methylparaben, phenol, phenoxyethanol, propylparaben, thimerosal, phenylmercuric acetate, phenylmercuric nitrate, benzalkonium chloride, chlorocresol, phenylmercuric salts, and methylhydroxybenzoate.

One reconstitution method includes quickly adding a diluent to a vessel containing a lyophilized daptomycin composition of Table 6, followed by swirling of the vessel if required. The diluent is preferably sWFI or sSCI. For example, the diluent can be added over a period of 1-60 seconds, more preferably 1-30 seconds and most preferably, the diluent is added in less than 20 seconds. Preferably, the weight of daptomycin in the composition to the volume of the diluent is in the range of 25 mg/mL to 200 mg/mL The parenteral pharmaceutical composition compositing daptomycin can be administered by intravenous infusion according to approved indications. For example, daptomycin for injection can be intravenously administered in 0.9% sodium chloride once every 24 hours for 7 to 14 days for the treatment of complicated skin and skin structure infections.

Compositions with Increased Daptomycin Chemical Stability

Figure 2:
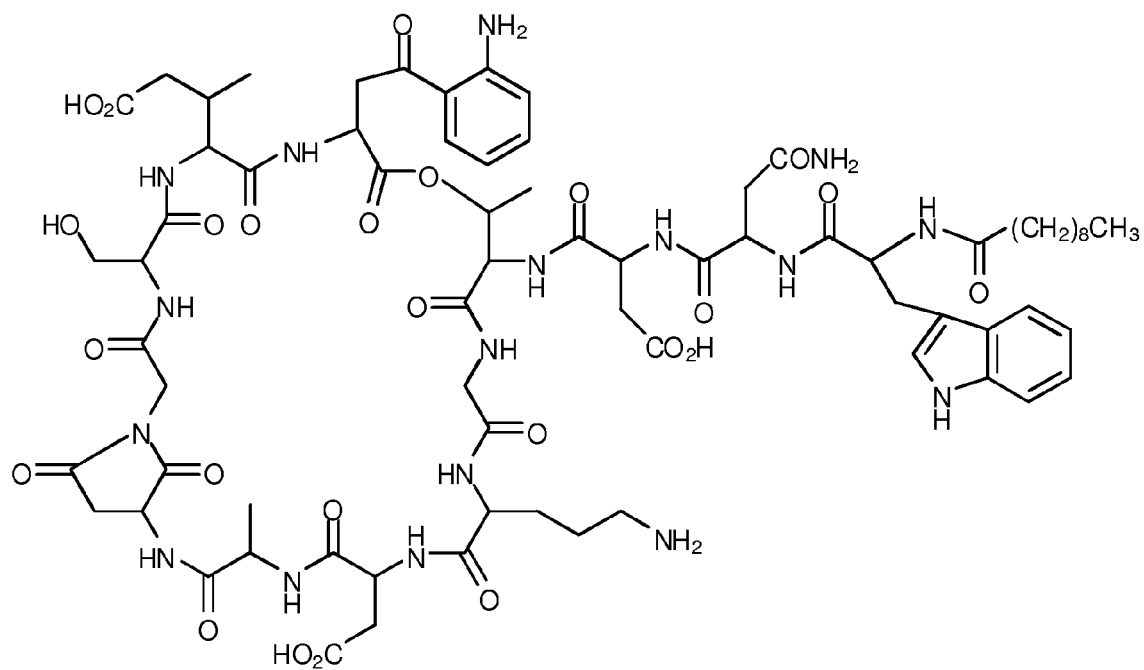
FIG. 2 is the chemical structure of anhydro-daptomycin.
Figure 4:
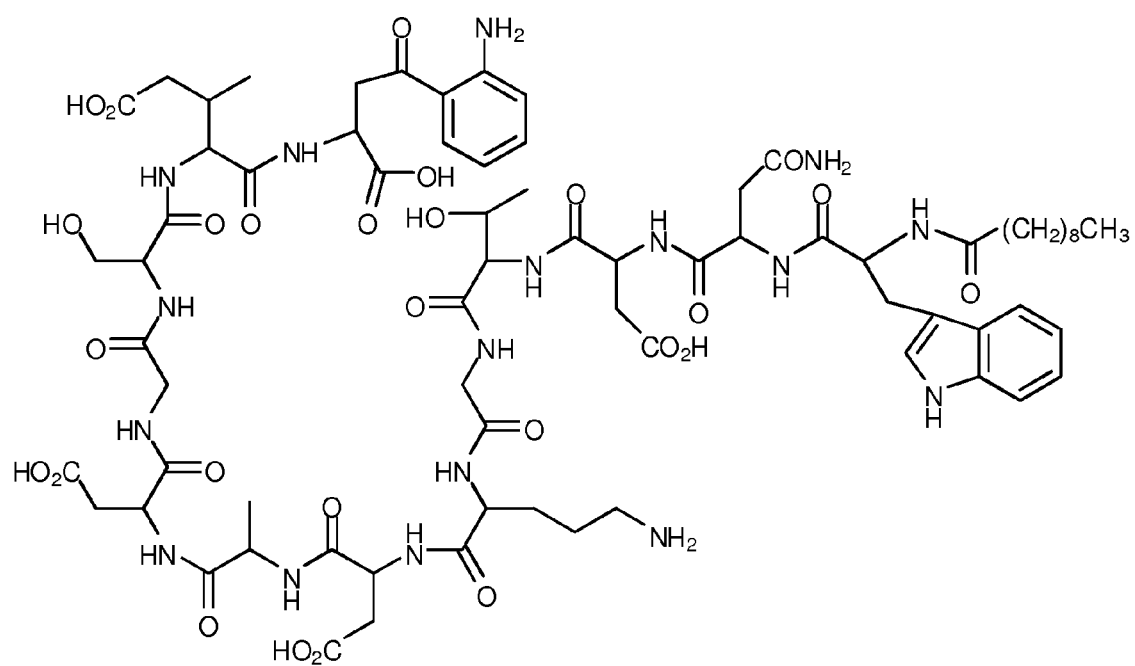
FIG. 4 is the chemical structure of the lactone hydrolysis product of daptomycin.

Unexpectedly, combining daptomycin with one or more non-reducing sugars (e.g., trehalose, sucrose and mannitol) in a solid pharmaceutical preparation enhanced the chemical stability of daptomycin in both solid and reconstituted liquid phases. Daptomycin chemical stabilities were measured by comparing measurements of total daptomycin purity from multiple solid samples stored under known time periods (e.g., up to 12 months) under known conditions (e.g., constant temperatures). The daptomycin total purity for each sample was measured by high performance liquid chromatography (HPLC) (using parameters in Table 3) according to Example 4. In addition, the amount of daptomycin (FIG. 1) in the reconstituted daptomycin solution was measured relative to the amount of substances selected from the group consisting of the anhydro-daptomycin (FIG. 2), the beta-isomer of daptomycin (FIG. 3) and the lactone hydrolysis product of daptomycin (FIG. 4). Similarly, to determine daptomycin chemical stability in the reconstituted daptomycin solution, the HPLC measurement and calculation of daptomycin purity in the reconstituted daptomycin solution was repeated according to Example 4 at various time intervals up to 14 days after preparing the reconstituted daptomycin solution.

In one aspect, a solid pharmaceutical daptomycin preparation having increased daptomycin stability can include daptomycin and a non-reducing sugar in an amount effective to increase the total daptomycin stability in the solid daptomycin preparation, as measured by total daptomycin purity according to Example 4. In another aspect, a solid pharmaceutical daptomycin preparation having increased daptomycin stability can include daptomycin and a non-reducing sugar in an amount effective to decrease the amount of substances selected from the group consisting of the anhydro-daptomycin (FIG. 2), the beta-isomer of daptomycin (FIG. 3) and the lactone hydrolysis product of daptomycin (FIG. 4) in the daptomycin preparation (as measured by Example 4) as a solid and/or in a liquid reconstituted form compared to the stability of a daptomycin preparation without glycine or a sugar.

The solid pharmaceutical daptomycin preparation having increased daptomycin stability can include daptomycin and a sugar in an amount effective to increase the chemical stability of daptomycin as measured by changes in total purity of daptomycin in the daptomycin preparation as a solid form compared to a daptomycin preparation without glycine or a sugar, where the daptomycin purity is measured according to Example 4.

As described in Example 5, solid lipopeptide compositions with increased lipopeptide chemical stability include a non-reducing sugar (e.g., such as sucrose or trehalose) or a combination of non-reducing sugars (e.g., sucrose and trehalose). The purity of daptomycin in each solid daptomycin pharmaceutical preparation was measured after reconstitution according to Example 4 (or the reconstituted solution was frozen and the daptomycin purity according the Example 4 was later determined after thawing the reconstituted solution). The solid pharmaceutical daptomycin formulations including non-reducing sugars can have more daptomycin (FIG. 1) upon reconstitution relative to substances selected from the group consisting of the anhydro-daptomycin (FIG. 2), the beta-isomer of daptomycin (FIG. 3) and the lactone hydrolysis product of daptomycin (FIG. 4). Preferred solid pharmaceutical daptomycin preparations with a non-reducing sugar have an increased daptomycin purity (and increased shelf stability) for a period of at least up to 6 months compared to solid daptomycin preparations without a non-reducing sugar. As described in Example 5, solid daptomycin preparations were stored in vials for a various time periods (e.g., 1 month, 2 months, 3 months and 6 months) at various temperatures ranges (e.g., 2-8 degrees C., 25 degrees C. and 40 degrees C.), followed by reconstitution of the solid preparation followed by detection of the amount of daptomycin and substances structurally similar to daptomycin in the reconstituted liquid composition as described in Example 4.

As described in Example 6, daptomycin in reconstituted liquid pharmaceutical daptomycin preparations containing non-reducing sugar(s) unexpectedly showed improved chemical stability than reconstituted daptomycin preparations without any sugar. The increased chemical stability in reconstituted daptomycin formulations containing non-reducing sugars was measured by differences in total daptomycin purity measurements according to Example 4 for up to 14 days on samples stored at temperatures of 5 degrees C., 25 degrees C. and 40 degrees C. For example, the purity of daptomycin (measured and calculated according to Example 4) in refrigerated (e.g., 2-10 degrees C.) reconstituted daptomycin preparations containing about 15.0-20.0% sucrose was unexpectedly greater over a period of up to 14 days compared to reconstituted daptomycin formulations without any sugar. The reconstituted daptomycin preparations can be combined with one or more pharmaceutically acceptable diluent to obtain a pharmaceutical composition for parenteral administration (e.g., formed or stored in vessels for intravenous administration such as bags or syringes).

To assess daptomycin chemical stability in the reconstituted solution, the purity of daptomycin was measured at multiple time intervals after reconstitution (or thawing if frozen), including time periods of up to 14 days (3, 7 and 14 days). The chemical stability of daptomycin in the reconstituted liquid composition was measured after various durations as described in Example 6, by measuring daptomycin purity according to Example 4. Compositions with increased daptomycin chemical stability had higher detected amounts of daptomycin relative to detected total amounts of the substances structurally similar to daptomycin in FIGS. 2-4 (as measured by the method of Example 4) than compositions with lower daptomycin chemical stability.

Solid daptomycin preparations with improved chemical stability (as solids and/or in reconstituted liquids) were prepared by combining daptomycin with non-reducing sugars including sucrose and trehalose and combinations of non-reducing sugars, such as sucrose and mannitol.

In some embodiments of the solid and liquid daptomycin preparations include at least 92%, at least 93%, at least 94%, at least 95%, at least 96%, at least 97% or at least 98% pure daptomycin as measured by Example 4. Preferably, solid pharmaceutical daptomycin preparations are characterized in that at least 92%, at least 93%, at least 94%, at least 95%, at least 96%, at least 97% or at least 98% of the total HPLC peak area detected at 214 nm according to Table 3 is obtained from daptomycin in a reconstituted form of the solid pharmaceutical daptomycin preparation according to the procedure of Example 4.

In some solid pharmaceutical daptomycin preparations, at least 92%, at least 93%, at least 94%, at least 95%, at least 96%, at least 97% or at least 98% by weight of the preparation consists of daptomycin, and glycine or one or more non-reducing sugars, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 2 minutes.

A preferred solid daptomycin preparation having increased reconstitution and increased daptomycin stability in powder and reconstituted forms includes a solid daptomycin preparation including daptomycin, sucrose, and a phosphate buffering agent; wherein a. the solid daptomycin preparation includes at least 92% pure daptomycin, as calculated by the ratio of absorbance (area under curve) at 214 nm for the daptomycin divided by the total area under the curve measured by high performance liquid chromatography (HPLC) of the reconstituted daptomycin solution at 214 nm according to Table 3; and b. the solid daptomycin preparation is obtainable by:
   i. forming an aqueous daptomycin solution including 105 mg/mL (10.5% w/v) daptomycin, a 7.1 mg/mL (50 mM) sodium phosphate dibasic buffering agent and 150 mg/mL (15% w/v) sucrose at a pH of about 7.0; and
   ii. converting the aqueous daptomycin formulation to the solid daptomycin preparation.

Preferred solid daptomycin preparations are obtained from daptomycin solutions including, about 2.5-25.0% w/v of one or more non-reducing sugars (e.g., sucrose, trehalose, and mannitol), and optionally further including one or more buffering agents such as sodium phosphate dibasic. Particularly preferred solid daptomycin preparations can be prepared by lyophilizing or spray drying liquid solutions containing daptomycin and sucrose (and optionally further containing about 50 mM sodium phosphate dibasic) at a pH of about 4.5 to 7.0 (including, e.g., pH values of 4.7-7.0).

Articles of manufacture containing the solid daptomycin preparation are also provided (e.g., enclosed sealed vials with a means for injecting the aqueous diluent into the vial, such as a self-sealing puncturable membrane), as well as products containing a daptomycin product formulated for parenteral administration and including the solid daptomycin preparation dissolved in an aqueous diluent (e.g., a bag or syringe adapted for intravenous administration of the daptomycin product).

Preferably, 500 mg of the solid pharmaceutical daptomycin composition dissolves in 10 mL of 0.9% aqueous sodium chloride in 1 minute or less at 25 degrees C. The pH of the aqueous solution of daptomycin can be adjusted to a pH of at least 4.7 prior to dissolving the non-reducing sugar in the aqueous solution with daptomycin. Optionally, the daptomycin preparation is prepared by adding a buffering agent to the aqueous solution of daptomycin before dissolving the non-reducing sugar in the aqueous solution with daptomycin. The liquid daptomycin formulation can have a daptomycin concentration of about 105 mg/mL. The sugar in the liquid daptomycin formulation can be selected from the group consisting of trehalose, sucrose, mannitol, lactose, maltose, fructose, dextrose, and combinations thereof. In one preferred example, 500 mg of the solid pharmaceutical daptomycin composition dissolves in 10 mL of 0.9% aqueous sodium chloride in 1 minute or less at 25 degrees C., and the solid pharmaceutical daptomycin preparation is prepared by:
   a. forming an aqueous solution of daptomycin at a pH of about 4.7-5.0;
   b. adding a buffering agent comprising phosphate, citrate, maleate or a combination thereof to the aqueous solution of daptomycin;
   c. dissolving a non-reducing sugar in the aqueous solution with daptomycin to form a buffered daptomycin sugar formulation;
   d. adjusting the pH of the buffered daptomycin sugar formulation to about 7.0; and
   e. lyophilizing the buffered daptomycin sugar formulation to form the solid pharmaceutical daptomycin composition.

Other examples of solid pharmaceutical daptomycin preparations can be prepared by:
   a. forming an aqueous solution of daptomycin at a pH of about 4.7-5.0;
   b. adding a buffering agent comprising phosphate, citrate, maleate or a combination thereof to the aqueous solution of daptomycin;
   c. dissolving a sugar in the aqueous solution with daptomycin to form a daptomycin sugar formulation, the sugar selected from the group consisting of trehalose, sucrose, mannitol, lactose, maltose, fructose, dextrose, and combinations thereof;
   d. adjusting the pH of the daptomycin sugar formulation to about 7.0; and
   e. lyophilizing the daptomycin sugar formulation to form the solid pharmaceutical daptomycin composition.

Methods of manufacturing a lyophilized daptomycin medicament preparation having an accelerated reconstitution time in an aqueous 0.9% aqueous sodium chloride diluent can include the following steps:
   a. forming an aqueous solution of daptomycin at a pH of about 4.7-5.0;
   b. adding a buffering agent comprising phosphate, citrate, maleate or a combination thereof to the aqueous solution of daptomycin;
   c. dissolving a sugar in the aqueous solution with daptomycin to form a buffered daptomycin sugar formulation containing about 2.5% to about 25% of the sugar, the sugar selected from the group consisting of trehalose, sucrose, mannitol, lactose, maltose, fructose, dextrose, and combinations thereof;
   d. adjusting the pH of the buffered daptomycin sugar formulation to about 6.5 to 7.5; and
   e. lyophilizing the buffered daptomycin sugar formulation to form the solid pharmaceutical daptomycin composition.

Preferably, 500 mg of the lyophilized daptomycin composition dissolves in 10 mL of 0.9% aqueous sodium chloride in 1 minute or less at 25 degrees C. The buffered daptomycin sugar formulation preferably includes a phosphate and about 2.5% to about 25% of the sugar.

EXAMPLES

The following examples are illustrative and do not limit the inventions described herein.

Improved daptomycin solid preparations were obtained by (a) forming a solid pharmaceutical preparation from a solution containing daptomycin and one or more sugars or glycine as described in Examples 2a and 2b, and (b) converting the daptomycin solution to a solid pharmaceutical preparation (e.g., by lyophilizing or spray drying), as described in Example 3. The solid pharmaceutical preparation can later be reconstituted by adding an aqueous diluent to dissolve the solid pharmaceutical preparation in about 4 minutes or less. Preferably, the solid pharmaceutical daptomycin preparations dissolve in the aqueous diluent in about 1 minute or less at 25 degrees C. (optionally with gentle stirring).

According to the package insert for daptomycin for injection sold under the trademark CUBICIN® (i.e., daptomycin without glycine or a sugar):
   "The contents of a CUBICIN® 500 mg vial should be reconstituted using aseptic technique as follows:
   Note: To minimize foaming, AVOID vigorous agitation or shaking of the vial during or after reconstitution.
   1. Remove the polypropylene flip-off cap from the CUBICIN® vial to expose the central portion of the rubber stopper.
   2. Slowly transfer 10 mL of 0.9% sodium chloride injection through the center of the rubber stopper into the CUBICIN® vial, pointing the transfer needle toward the wall of the vial.
   3. Ensure that the entire CUBICIN® product is wetted by gently rotating the vial.
   4. Allow the product to stand undisturbed for 10 minutes.

5. Gently rotate or swirl the vial contents for a few minutes, as needed, to obtain a completely reconstituted solution."

In contrast, the improved daptomycin solid preparations reconstitute faster in an aqueous diluent than daptomycin without sugar or glycine. Particularly preferred solid preparations can be reconstituted in an aqueous diluent in less than 2 minutes at 25 degrees C., more preferably in less than about 1 minute at 25 degrees C. Table 6 (FIG. 5) and Table 5 (FIG. 6) provide reconstitution times for various solid daptomycin preparations, obtained by measuring the time required to dissolve 500 mg of the solid daptomycin preparation in 10 mL of a 0.9% aqueous sodium chloride diluent at about 25 degrees C.

In addition, the Examples describe improved daptomycin solid preparations that provide greater daptomycin chemical stability in a solid form as described in Example 5 and in the reconstituted liquid form as described in Example 6. The improved daptomycin preparations can include more daptomycin relative to substances selected from the group consisting of the anhydro-daptomycin (FIG. 2), the beta-isomer of daptomycin (FIG. 3) and the lactone hydrolysis product of daptomycin (FIG. 4), as measured by the HPLC method of Example 4. Preferably, the solid daptomycin preparation is obtained by converting a liquid daptomycin solution to a solid form, subsequently reconstituting the solid form according to Example 4, and measuring a total HPLC peak area at 214 nm according to HPLC parameters in Table 3 in the reconstituted liquid that is at least at least 92% obtained from daptomycin in the reconstituted solution. The solid daptomycin preparation can consist of daptomycin, one or more sugars selected from the group consisting of sucrose, trehalose, and mannitol, pharmaceutically appropriate salts (e.g., sodium chloride), one or more buffering agents such as sodium phosphate dibasic and materials providing up to 8% of the total HPLC peak area at 214 nm according to HPLC parameters in Table 3 in the reconstituted liquid formed according to Example 4.

Table 8 (FIG. 7) describes various daptomycin pharmaceutical compositions. In Table 8, the designation "Molar Ratio of existing components, respectively" refers to the molar ratio of daptomycin to the other components listed as [B], [C] and [D] (when present), in that order. For example, if the composition comprises daptomycin [A] and one excipient [B], the molar ratio will be expressed as [A]:[B]. If the composition comprises two excipients [B] and [C], than the molar ratio will be expressed as daptomycin [A]:excipient [B]:excipient [C] and so on. If the composition comprises daptomycin [A], and excipient [B] and a buffering agent [D], the molar ratio will be expressed as [A]:[B]:[D].

Table 6 (FIG. 5) provides non-limiting examples of daptomycin compositions that reconstitute in an aqueous diluent in less than 2 minutes. Table 7 (FIG. 6) provides examples of other daptomycin compositions that reconstitute in an aqueous diluent in about 2 minutes or more. Daptomycin compositions without sugar or glycine in Table 6 and Table 7 were obtained by either Method A (Example 1a) or Method B (Example 1b) followed by lyophilization according to Example 3. Daptomycin compositions with sugar or glycine in Table 6 and Table 7 were obtained by either Method A (Example 2a) or Method B (Example 2b) followed by lyophilization according to Example 3. Molar ratios in Tables 6 and 7 were calculated based on molecular weights in Table 1.

TABLE 1

| Molecular Weights of Daptomycin and Excipients | |
|---|---|
| Daptomycin | 1620.67 |
| Phosphate buffer | 141.96 |
| Sucrose | 342.3 |
| Lactose | 342.3 |
| Maltose | 342.12 |
| Trehalose | 180.16 |
| Fructose | 180.16 |
| Dextrose | 180.16 |
| Mannitol | 182.17 |
| Glycine | 75.07 |

The present invention will be further understood by reference to the following non-limiting examples. The following examples are provided for illustrative purposes only and are not to be construed as limiting the scope of the invention in any manner.

Example 1A

Comparative Preparation Method A (Lyophilize Daptomycin at pH 4.7 without a Sugar or Glycine)

Compounding of the comparative daptomycin formulation without sugar or glycine was performed under chilled (2-10° C.) conditions. Daptomycin Active Pharmaceutical Ingredient (API) was supplied as a frozen liquid at a concentration range of 125-130 mg/mL, pH 3.0. Compounding began by obtaining liquid daptomycin API (e.g., thawing of frozen daptomycin API provided at pH of about 3.0) followed by pH adjustment to the target pH of about 4.7 using 3N NaOH. The bulk solution was further diluted to the target concentration of 105 mg/mL with sWFI and mixed to ensure solution homogeneity (also at 2-10° C.). The bulk product solution was 0.2 µm filtered and filled into 10 mL vials followed by lyophilization according to the current lyophilization cycle as outlined in Example 3. The drug product formulation was stoppered under nitrogen and sealed.

Example 1B

Comparative Preparation Method B (Lyophilize Daptomycin at pH 7.0 without a Sugar or Glycine)

Compounding of the bulk formulation was performed under chilled (2-10° C.) conditions. Daptomycin API was supplied as a frozen liquid at a concentration range of 125-130 mg/mL, pH 3.0. Compounding of the bulk formulation utilized thawing of the API followed by pH adjustment to the target pH of 7.0 using 3N NaOH under chilled (2-10° C.) conditions, followed by dilution to the target concentration of 105 mg/mL with sWFI and mixing to ensure solution homogeneity. Formulated drug product was 0.2 µm filtered and filled into 10 mL vials followed by lyophilization according to a modified lyophilization cycle as outlined in Example 3. The drug product formulation was stoppered under nitrogen and sealed.

Example 2A

Preparation Method A (Lyophilize at pH 4.7)

Compounding of improved daptomycin formulation was performed under chilled (2-10° C.) conditions. Daptomycin Active Pharmaceutical Ingredient (API) was supplied as a frozen liquid at a concentration range of 125-130 mg/mL, pH 3.0. Compounding began by obtaining liquid daptomycin API (e.g., thawing of frozen daptomycin API provided at pH of about 3.0) followed by pH adjustment to the target pH of about 4.7 using 3N NaOH, followed by addition of sugar(s) (e.g., sucrose). The bulk solution was further diluted to the target concentration of 105 mg/mL with sWFI and mixed to ensure solution homogeneity (also at 2-10° C.). The bulk product solution was 0.2 μm filtered and filled into 10 mL vials followed by lyophilization according to the current lyophilization cycle as outlined in Example 3. The drug product formulation was stoppered under nitrogen and sealed. The sugars were added as either a powder or in a suitable solution, such as sWFI.

Example 2B

Preparation Method B (Lyophilize at pH 7.0)

Compounding of improved daptomycin formulations was performed under chilled (2-10° C.) conditions. Daptomycin API was supplied as a frozen liquid at a concentration range of 125-130 mg/mL, pH 3.0. Compounding of the bulk formulation utilized thawing of the API followed by pH adjustment to the target pH of 4.7 using 3N NaOH under chilled (2-10° C.) conditions, followed by addition of buffering agents (phosphate, citrate, etc.) with subsequent addition of glycine or sugar(s) (sucrose, trehalose, mannitol). Once the excipients (sugars, buffering agents) were completely dissolved the solution pH of 4.7 was adjusted to 7.0 with 3N NaOH and diluted to the target concentration of 105 mg/mL with sWFI and mixed to ensure solution homogeneity. Formulated drug product was 0.2 μm filtered and filled into 10 mL vials followed by lyophilization according to a modified lyophilization cycle as outlined in Example 3. The drug product formulation was stoppered under nitrogen and sealed.

Example 3

Lyophilization of Compositions Prepared by Methods A and B

Product vials were loaded into the lyophilizer at 5±4° C. and dispersed randomly across each shelf. The composition was lyophilized to dryness, back filled with nitrogen and stoppered under vacuum. Once stoppering was complete, the lyophilization unit was bled to atmospheric pressure, using filtered nitrogen, and the product vials were removed for capping with an aluminum seal. The cycle parameters for the various formulations are summarized in Table 2.

TABLE 2

Summary of lyophilization cycle parameters for various compositions

| Step No. | Cycle A<br>Formulations 1-8,<br>16, 17, 18, 70-79 | Cycle B<br>Formulations 9-11,<br>13-15, 19 | Cycle C<br>Formulations 12,<br>20-27 | Cycle D<br>Formulations 35,<br>45, 50-69 |
|---|---|---|---|---|
| 1 | Load product at 5° C. and hold for 60 minutes | Load product at 5° C. and hold for 60 minutes | Load product at 5° C. and hold for 60 minutes | Load product at 5° C. and hold for 60 minutes |
| 2 | Ramp shelf to −50° C. over 180 minutes and hold for 4 hours | Ramp shelf to −50° C. over 180 minutes and hold for 4 hours | Ramp shelf to −50° C. over 180 minutes and hold for 4 hours | Ramp shelf to −50° C. over 180 minutes and hold for 4 hours |
| 3 | Apply vacuum to 90 mTorr and maintain vacuum until stoppering occurs | Apply vacuum to 90 mTorr and maintain vacuum until stoppering occurs | Apply vacuum to 90 mTorr and maintain vacuum until stoppering occurs | Apply vacuum to 90 mTorr and maintain vacuum until stoppering occurs |
| 4 | Ramp shelf to −10° C. over 6 hours and hold for NLT[1] 40 hours | Ramp shelf to −17° C. over 6 hours and hold for NLT 40 hours | Ramp shelf to −25° C. over 6 hours and hold for NLT 40 hours | Ramp shelf to −15 °C. over 6 hours and hold for NLT 40 hours |
| 5 | Ramp shelf to 40° C. over 4 hours and hold for 6 hours | Ramp shelf to 40° C. over 4 hours and hold for 6 hours | Ramp shelf to 40° C. over 4 hours and hold for 6 hours | Ramp shelf to 40° C. over 4 hours and hold for 6 hours |
| 6 | Backflush chamber with nitrogen | Backflush chamber with nitrogen | Backflush chamber with nitrogen | Backflush chamber with nitrogen |
| 7 | Stopper vials at 12.5 psia and break vacuum | Stopper vials at 12.5 psia and break vacuum | Stopper vials at 12.5 psia and break vacuum | Stopper vials at 12.5 psia and break vacuum |

[1]NLT = not less than

Example 4

Measuring the Amount of Daptomycin and Substances Structurally Similar to Daptomycin Unless otherwise indicated, the amount of daptomycin and three compounds structurally similar to daptomycin (FIGS. 2-4) was measured using HPLC analysis in aqueous reconstituted liquid solutions containing daptomycin, using an Agilent 1100 or 1200 high performance liquid chromatography instrument with an ultraviolet (UV) detector. Peak areas were measured using Waters Empower2 FR5 SPF build 2154 software. Unless otherwise indicated, percent purity of a solid daptomycin preparation was determined by reconstituting 500 mg of the solid daptomycin preparation in 10 mL of an aqueous diluent to form a reconstituted daptomycin solution, then measuring the absorbance of the reconstituted sample at 214 nm by HPLC using the HPLC parameters of Table 3. The percent purity of daptomycin in the solid daptomycin preparation was calculated by the ratio of absorbance (area under curve) at 214 nm for the daptomycin divided by the total area under the curve measured by HPLC of the reconstituted daptomycin solution at 214 nm according to Table 3 and the formula below. For a 92% pure daptomycin sample, 92% of the total peak area from all peaks ≥0.05 area % was attributed to dapotmycin.

In addition, the amount of three substances structurally similar to daptomycin can be detected by HPLC at 214 nm according to Table 3: anhydro-daptomycin (FIG. 2), the beta-isomer of daptomycin (FIG. 3) and the lactone hydrolysis product of daptomycin (FIG. 4). Unless otherwise indicated, the amount of these substances in solid daptomycin preparations is measured by HPLC according to Table 3 upon reconstitution of 500 mg of the solid daptomycin preparation in 10 mL of an aqueous diluent to form a reconstituted daptomycin solution, then measuring the absorbance at 214 nm of the reconstituted daptomycin by HPLC using the parameters of Table 3.

TABLE 3

| | | |
|---|---|---|
| 1. | Solvent Delivery System: | |
| | Mode: | Isocratic pumping |
| | Flow rate: | 1.5 mL/min |
| | Run time: | 75 minutes |
| 2. | Solvent A: 50% acetonitrile in 0.45% $NH_4H_2PO_4$ at pH 3.25 | |
| | Solvent B: 20% acetonitrile in 0.45% $NH_4H_2PO_4$ at pH 3.25 | |
| | The target condition is approximately 45% Solvent A and 55% Solvent B to retain daptomycin at 36.0 ± 1.5 minutes; however, the solvent ratio may be adjusted to achieve the desired retention time. | |
| 3. | Autosampler cooler: | 5 (2 to 8) ° C. |
| 4. | Injection volume: | 20 μL |
| 5. | Column: | IB-SIL (Phenomenex), C-8-HC, 5 μ, 4.6 mm × 250 mm (or equivalent) |
| 6. | Pre-column: | IB-SIL (Phenomenex), C-8, 5 μ, 4.6 mm × 30 mm (or equivalent) |
| 7. | Detection wavelength: | 214 nm |
| 8. | Column Temperature: | 25 (22 to 28) ° C. |
| 9 | Integration: | A computer system or integrator capable of measuring peak area. |

The purity of daptomycin was calculated based on HPLC data, calculated as follows:
  Area % of individual substances structurally similar to daptomycin is calculated using the following equation:
  Area % of daptomycin and all substances structurally similar to daptomycin as determined using absorbance at 214 nm
  Calculate the area of daptomycin and all other peaks ≥0.05 area %, % area=$(A_i/A_{tot})$x100% where:
% area=Area % of an individual peak;
$A_i$=Peak of an individual peak; and
$A_{tot}$=total sample peak area including daptomycin.
  Area % of total substances structurally similar to daptomycin is calculated using the following equation:
  Area % of total substances structurally similar to daptomycin equals the sum of all reported area % values from the individual substances (sum of all impurities=/>0.05%)
  Calculate the % purity of daptomycin in Area % using the following equation:

% Daptomycin=100%−% total substances structurally similar to daptomycin.

Example 5

Measuring the Chemical Stability of Daptomycin in Solid Pharmaceutical Compositions This example shows increased daptomycin chemical stability of solid pharmaceutical daptomycin compositions in certain preferred compositions containing sucrose, mannitol, trehalose, and glycine compared to daptomycin compositions without sugar or glycine and daptomycin compositions with certain reducing sugars.

The chemical stability of various solid pharmaceutical daptomycin compositions was evaluated by placing the composition in vials at various temperatures (2-8 deg. C., 25 deg. C. and 40 deg. C.). The solid pharmaceutical daptomycin compositions were obtained by lyophilizing or spray drying liquid compositions prepared according to Example 2a (Method A, at pH 4.7) or Example 2b (Method B, at pH 7.0). Lyophilization was performed according to Example 3. The amount of daptomycin and three daptomycin-related impurities was measured using the HPLC method of Example 4 in reconstituted solutions formed by dissolving about 500 mg of solid daptomycin preparations in 10 mL of 0.9% aqueous sodium chloride. The total daptomycin purity calculated according to Example 4 was plotted for measurements at 0, 1, 2, 3 and 6 months for vials of various solid pharmaceutical daptomycin compositions maintained at 40 deg. C. The slope of linear regression best fit to the plot of total daptomycin purity per month was calculated for each solid pharmaceutical daptomycin formulation (slope in % total daptomycin purity/month).

The data in Table 4 shows the ratio of the slopes for each solid daptomycin preparation normalized to the slope obtained from reconstituted solid daptomycin for injection, which does not contain sucrose. Referring to Table 4, ratios under column A were obtained from solid preparations prepared according the Method A in Example 2a (i.e., obtained from solutions containing daptomycin at a pH of 4.7), while ratios under column B were obtained from solid preparations prepared according to the Method B in Example 2b (i.e., obtained from solutions containing daptomycin at a pH of 7.0 that further contain 50 mM of a sodium phosphate buffering agent). Ratios with a "*" were from solid daptomycin preparations originally converted into solids by spray drying; all other samples were obtained from solid daptomycin preparations originally converted into solids by lyophilization (Example 3). Entries with "NT" in Table 4 were not tested. All ratios in Table 4 were obtained from linear regression of measurements of total purity of daptomycin (FIG. 1) relative to substances structurally similar to daptomycin shown in FIGS. 2-4 at 0 (i.e., after formation of the solid material), 1 month, 2 months, 3 months and 6 months of storage at 40 deg. C., where the amount of daptomycin and substances structurally similar to daptomycin were detected and calculated according to Example 4. The ratios in Table 4 represent changes in the rate of daptomycin total purity relative to daptomycin for injection (normalized to 1.00 for Method A and Method B preparations). Ratios below 1.00 represent reduced rates in the reduction of daptomycin total purity, or increased chemical stability of the daptomycin in a formulation relative to the daptomycin chemical stability absent sucrose in the daptomycin for injection product. Accordingly, the lower the ratio in Table 4, the more stable the daptomycin in the corresponding formulation in relation to the substances structurally similar to daptomycin in FIGS. 2-4.

TABLE 4

Ratio of % Change in Daptomycin Total Purity per Month Relative to Daptomycin for Injection (6 months)

| Formulation (% w/v in solution prior to lyophilization or spray drying) | Synthesis Method Ex 2A | Synthesis Method Ex 2B |
|---|---|---|
| 15.0% Sucrose | 0.16 | 0.04 |
| 15.0% Sucrose* | NT | 0.04 |
| 15.0% Sucrose | NT | 0.10 |
| 5.0% Sucrose + 3.0% Mannitol | 0.48 | 0.10 |
| 10.0% Sucrose + 3.0% Mannitol | 0.22 | 0.13 |
| 20.0% Sucrose | 0.22 | 0.13 |
| 10.0% Sucrose | 0.21 | 0.15 |

TABLE 4-continued

Ratio of % Change in Daptomycin Total Purity per
Month Relative to Daptomycin for Injection (6 months)

| Formulation (% w/v in solution prior to lyophilization or spray drying) | Synthesis Method Ex 2A | Synthesis Method Ex 2B |
|---|---|---|
| 5.0% Sucrose + 6.0% Mannitol | 0.45 | 0.16 |
| 2.5% Sucrose + 3.0% Mannitol | 0.60 | 0.17 |
| 2.5% Sucrose + 6.0% Mannitol | 0.56 | 0.18 |
| 10.0% Sucrose + 6.0% Mannitol | 0.24 | 0.20 |
| 25.0% Trehalose | 0.41 | 0.22 |
| 10.0% Trehalose | 0.47 | 0.26 |
| 6.0% Mannitol | 0.95 | 0.27 |
| 5.0% Sucrose | 0.35 | 0.27 |
| 2.5% Sucrose | 0.61 | 0.32 |
| 5.0% Trehalose | 0.67 | 0.35 |
| 2.5% Trehalose | NT | 0.42 |
| 5% Glycine | 0.97 | 0.74 |
| Daptomycin (No Sugar or Glycine) | 1.00 | 1.00 |
| 20% Lactose | 2.02 | 1.01 |
| 2.5% Lactose | 2.85 | 1.19 |
| 2.5% Maltose | 2.73 | 1.28 |
| 5% Maltose | 2.29 | 1.37 |
| 5% Lactose | 2.44 | 1.41 |
| 2.5% Fructose | NT | 1.41 |
| 5% Fructose | NT | 1.57 |
| 5% Dextrose:Fructose | 7.03 | 2.66 |
| 2.5% Dextrose:Fructose | 8.11 | 2.69 |
| 5% Dextrose | 8.08 | 3.38 |
| 2.5% Dextrose | 9.90 | 3.51 |
| 15.0% Sucrose + 3.0% Mannitol | 0.14 | NT |
| 15.0% Sucrose + 6.0% Mannitol | 0.25 | NT |
| 17.5% Trehalose | 0.31 | NT |

NT = not tested
*= prepared by spray drying, not lyophilization

The data in Table 4 show that daptomycin in a solid pharmaceutical daptomycin composition containing 15.0% sucrose showed about a 84% increase in daptomycin chemical stability compared to the daptomycin for injection in formulations prepared according to Method A (Example 2a), and a 96% increase in daptomycin chemical stability compared to the daptomycin for injection in formulations prepared according to Method B (Example 2b). Similarly, the solid pharmaceutical daptomycin containing 20.0% sucrose showed increases in daptomycin chemical stability relative to daptomycin without sucrose (i.e., daptomycin for injection) of about 78% (Method A) and 87% (Method B). Thus, combining 15-20% sucrose to a lyophilized daptomycin composition increased daptomycin chemical stability by at least 78%, and as much as 96%. In contrast, Table 4 also shows that daptomycin was about 2-9 times less stable in formulations comprising daptomycin and lactose, maltose, fructose, and/or dextrose. Table 4 therefore shows that daptomycin prepared by Methods of Example 2a and 2b (Methods A and B respectively) was stabilized when combined with non-reducing sugars or glycine (relative to daptomycin without a sugar or glycine), while daptomycin was less stable in formulations containing reducing sugars.

FIG. 8 is Table 9 showing the percent change in total daptomycin purity measured and calculated for various daptomycin formulations according to Example 4. Recitation of "PO4" in Table 9 refers to formulations that contain sodium phosphate dibasic buffer agent. Recitation of a "pH" value in Table 9 refers to the pH at which the formulation was compounded (i.e., the pH of the daptomycin formulation solution that was lyophilized to form the solid daptomycin formulations that were tested to obtain the data in Table 9). NT=not tested.

To obtain the data in Table 9, each solid daptomycin formulation was maintained at 40 degrees C. for various time periods (1, 2, 3, or 6 months), before reconstituting the solid daptomycin formulation and measuring the daptomycin purity according to the method of Example 4.

Table 9 shows the Daptomycin Stability Ratio, calculated as follows:

1. Prepare a control sample (daptomycin for injection commercial product, without sugar or glycine) compounded according to Example 1b and measure according to Example 4 the total percent daptomycin purity for the control sample after formulation
2. Measure the total percent daptomycin purity for a control sample according to Example 4 after storing the control sample for a given time period at 40 degrees C. and subtract the total percent daptomycin purity after storage for that time period from the total daptomycin purity after formulation to provide a Total Control Percent Purity Loss;
3. Measure the total percent daptomycin purity of each formulation according to Example 4 after storing the formulation for a time period at 40 degrees C. (e.g., 1 month, 2 months, etc.) and subtract the total percent purity after storage for that time period from the total daptomycin purity of the control sample after formulation to provide a Total Formulation Daptomycin Percent Purity Loss;
4. Calculate the Daptomycin Stability Ratio at 40 degrees C. by dividing Total Formulation Daptomycin Percent Purity Loss obtained for each formulation after the same storage time period (from step 3) by the Total Control Percent Purity Loss (from step 2) after a given storage time period:

$$\text{Daptomycin Stability Ratio} = \frac{\text{Total Formulation Daptomycin Percent Purity Loss Measured by Step 3}}{\text{Total Control Daptomycin Percent Purity Loss Measured by Step 2}}$$

Steps 2-4 are repeated to calculate each Daptomycin Stability Ratio. The Daptomycin Stability Ratio is calculated with a separate control sample that has been stored for the same time period as the formulation. For example, Daptomycin Stability Ratio values calculated for a formulation after 1 month storage time at 40 degrees C. were obtained by dividing the value from step 3 for the formulation by the value obtained from step 2 for a control that was stored for 1 month at 40 degrees C. (i.e., the same storage period and storage conditions as the formulation analyzed in step 3). Similarly, Daptomycin Stability Ratio values at 2 months would be calculated with a control sample that was stored for 2 months under the same conditions as the formulation used in step 3.

Daptomycin Stability Ratio values less than 1.000 in Table 9 indicate that the corresponding formulation has a higher daptomycin chemical stability measured as a greater total daptomycin percent purity (measured by Example 4) in the sample formulation than in the control sample of daptomycin without sugar or glycine (compounded according to step 1 above) after the corresponding storage period at 40 degrees C. Preferred compositions have Daptomycin Stability Ratios of less than 0.800, more preferably less than 0.500, and most preferably Daptomycin Stability Ratios of less than 0.300.

The data in Table 9 shows that daptomycin was generally more chemically stable (as measured by daptomycin improved purity according to Example 4 upon reconstitution in aqueous diluent) for daptomycin compositions containing a non-reducing sugar compounded at pH 7.0 with a buffering agent than for daptomycin without a sugar. Notably, the formulations comprising 15% sucrose compounded according to Method A (Example 2a) or Method B (Example 2b) provided very high levels of daptomycin chemical stability among the samples tested, and significantly higher levels of daptomycin chemical stability over 12 months than observed for daptomycin of comparative formulation 0 without a sugar or glycine. The sucrose-mannitol formulations also provided improvement in daptomycin chemical stability over the daptomycin comparative formulation 0 without sugar or glycine. For example the 10% sucrose/3% mannitol, 10% sucrose/6% mannitol, and 15% sucrose/6% mannitol all compounded according to Method A (Example 2a) provided significantly improved daptomycin stability. in contrast to the 15% sucrose/6% mannitol formulations compounded according to Method A (Example 2a). The 5% glycine formulation prepared according the Method B (Example 2b) also provided significant daptomycin stabilization, while the corresponding 5% glycine preparation from Method A (Example 2a) was less stable than daptomycin without sugar or glycine (Formulation 0). All daptomycin formulations in Table 9 containing sucrose showed increased daptomycin chemical stability compared to daptomycin without a sugar or glycine in the comparator formulation 0 (as measured by Example 4).

Example 6

Measuring the Chemical Stability of Daptomycin in Liquid Reconstituted Pharmaceutical Compositions This example shows increased daptomycin chemical stability in reconstituted pharmaceutical daptomycin compositions in compositions containing sucrose compared to comparable compositions without sucrose.

The chemical stability of various liquid pharmaceutical daptomycin compositions was evaluated by placing the composition in vials at various temperatures (5 deg. C., and 40 deg. C.). The liquid reconstituted pharmaceutical daptomycin compositions were obtained by reconstituting about 500 mg of solid daptomycin preparations in 10 mL of sWFI. Each solid daptomycin preparation was obtained by lyophilizing or spray drying liquid compositions prepared according to Example 1 (Method A, at pH 4.7) or Example 2 (Method B, at pH 7.0). Lyophilization was performed according to Example 3. The amount of daptomycin and daptomycin-related impurities was measured using the HPLC method of Example 4 in reconstituted solutions formed by dissolving. The % daptomycin was measured and calculated according to Example 4 for measurements at 0, 3, 7 and 14 days for vials of various solid pharmaceutical daptomycin compositions maintained at 5 deg. C. or 40 deg. C.

The data in Table 5 shows the amount of % daptomycin at each measurement normalized to the % daptomycin obtained from reconstituted solid daptomycin for injection, which does not contain sucrose. Referring to Table 5, each sample was reconstituted from a solid pharmaceutical daptomycin composition prepared by Method A in Example 1 (i.e., obtained from solutions containing daptomycin at a pH of 4.7) or Method B in Example 2 (i.e., obtained from solutions containing daptomycin at a pH of 7.0 that further contain 50 mM of a sodium phosphate buffering agent), as indicated in the "Method" column. The temperature in degrees C. of the reconstituted liquid is indicated under "Temp (deg C.)." Numbers below 1.000 in Table 5 indicate a lower % daptomycin purity than daptomycin for injection at 0 days for a given temperature. All entries are normalized to the measurement for daptomycin for injection at the corresponding temperature (e.g., all measurements taken at 5 degrees C. are normalized to the % daptomycin measured for daptomycin for injection at 5 degrees C.). Accordingly, the closer the number in Table 5 is to 1.000, the more stable the daptomycin is in the reconstituted liquid form in the corresponding formulation in relation to the substances structurally similar to daptomycin in FIGS. 2-4.

TABLE 5

% Daptomycin Measured In Reconstituted Solution

| | Method | Temp (deg C.) | 0 | 3 days | 7 days | 14 days |
|---|---|---|---|---|---|---|
| Daptomycin for Injection | A | 5 | 1.0000 | 0.9957 | 0.9900 | 0.9822 |
| 15.0% Sucrose | B | 5 | 0.9998 | 1.0003 | 0.9974 | 0.9977 |
| 6.0% Mannitol | B | 5 | 1.0003 | 0.9998 | 0.9992 | 0.9974 |
| Daptomycin for Injection | A | 25 | 1.0000 | 0.9394 | 0.8618 | 0.7410 |
| 15.0% Sucrose | B | 25 | 0.9998 | 0.9844 | 0.9609 | 0.9184 |
| 6.0% Mannitol | B | 25 | 1.0003 | 0.9846 | 0.9609 | 0.9196 |
| Daptomycin for Injection | A | 40 | 1.0000 | 0.6711 | 0.4145 | NT |
| 15.0% Sucrose | B | 40 | 0.9998 | 0.8752 | 0.7241 | NT |
| 6.0% Mannitol | B | 40 | 0.9996 | 0.8753 | 0.7207 | NT |

NT = not tested

The data in Table 5 shows that the total % daptomycin in a liquid reconstituted pharmaceutical daptomycin composition containing 15.0% sucrose was significantly more stable than daptomycin for injection (without sucrose) at 25 degrees C. after 14 days (0.9184 for the sucrose formulation compared to 0.7410 for the daptomycin for injection formulation without sucrose). This represents about a 23% increase in daptomycin chemical stability in the reconstituted solution in the presence of the reconstituted composition consisting essentially of daptomycin, about 15% sucrose, and 50 mM sodium phosphate. Accordingly, the 15.0% sucrose formulation of daptomycin demonstrated a surprisingly enhanced room temperature daptomycin chemical stability and improved shelf life after reconstitution.

Additional Exemplary Embodiments

Some specific embodiments of the invention supported by the examples include the following:
1. A solid pharmaceutical composition comprising daptomycin and glycine or a non-reducing sugar, wherein the composition has an increased rate of reconstitution, an increased rate of reconstitution being characterized by a dissolution of 500 mg of the composition in 10 mL of 0.9% aqueous sodium chloride under gentle swirling at 25 degrees C. in 5 minutes or less, in particular less than 2 minutes or less than 1 minute.
2. Pharmaceutical composition of specific embodiment 1 wherein the composition has increased reconstitution chemical stability in comparison to lyophilized daptomycin, reconstitution taking place in 0.9% aqueous sodium chloride at 25 degrees C., wherein increased reconstitution chemical stability is characterized by an amount of daptomycin relative to the anhydro-daptomycin (FIG. 2), the beta-isomer of daptomycin (FIG. 3) and/or the lactone hydrolysis product of daptomycin (FIG. 4) that is higher than the corresponding amount for lyophilized daptomycin.
3. Pharmaceutical composition according to any of specific embodiments 1 to 2 wherein the composition has increased storage chemical stability in comparison to lyophilized daptomycin, wherein the increased storage chemical stability is characterized by an amount of daptomycin relative to the anhydro-daptomycin (FIG. 2), the beta-isomer of daptomycin (FIG. 3) and/or the lactone hydrolysis product of daptomycin (FIG. 4) which is higher than the corresponding amount for lyophilized daptomycin when reconstituting both samples in 0.9% aqueous sodium chloride after storage of the compositions for at least 3 months at 40° C. under a nitrogen atmosphere.

4. Pharmaceutical composition according to any of specific embodiments 1 to 4 wherein the composition is produced by a process comprising:
a. forming an aqueous daptomycin solution comprising daptomycin, a buffering agent, and a non-reducing sugar or mixtures thereof; or glycine and adjusting the pH to about 5 to 8, in particular 6.5 to 7.5 or about 7, and
b. converting the aqueous daptomycin solution to the solid composition, in particular by lyophilization.

5. Pharmaceutical composition according to any of specific embodiments 1 to 5 wherein the composition comprises a non-reducing sugar or mixtures thereof, in an amount effective for decreasing the rate of daptomycin degradation in comparison to a substantially identical composition lacking said non-reducing sugar, wherein the rate of degradations are defined as the respective loss of daptomycin after storage of the compositions for at least 3 months at 40° C. under a nitrogen atmosphere.

6. Pharmaceutical composition according to any of specific embodiments 1 to 6 wherein the sugar is selected from non-reducing disaccharides, sugars that are substantially amorphous upon lyophilization, sucrose, dextranes, trehalose, mannitol, sorbitol or combinations thereof.

7. Pharmaceutical composition according to any of specific embodiments 1 to 7 wherein the sugar or glycine is used in amounts of about 1 to 40 wt.-%, in particular about 5-20 wt.-% or about 15 wt.-%, on basis of the weight of the total composition.

8. Liquid pharmaceutical composition comprising daptomycin and a sugar selected from sucrose, trehalose, mannitol or mixtures thereof, in an amount effective for decreasing the rate of daptomycin degradation in comparison to a solution obtained by reconstituting lyophilized daptomycin in 0.9% aqueous sodium chloride, wherein the rate of degradations are defined as the respective loss of daptomycin after storage of the liquid compositions for at least 7 days at 25 degrees C.

9. Method for preparing a composition according to any one of specific embodiments 1 to 8 comprising:
a. supplying a daptomycin preparation;
b. adding at least one excipient, optionally selected from sorbitol, mannitol, sucrose, glycine, trehalose, lactose, maltose, fructose and dextrose;
c. optionally adding a pH adjuster to obtain the desired pH;
d. optionally diluting the solution of step c with sWFI;
e. optionally filtering the solution of step d; and
f. converting the composition to a powdered form.

10. A solid pharmaceutical composition comprising daptomycin and glycine or a non-reducing sugar, wherein the composition has an increased rate of reconstitution, an increased rate of reconstitution being characterized by a dissolution of 500 mg of the composition in 10 mL of 0.9% aqueous sodium chloride under gentle swirling at 25 degrees C. in 5 minutes or less, in particular less than 2 minutes or less than 1 minute; and where the solid pharmaceutical composition is further characterized in that the daptomycin preparation has a lower amount of one or more substances selected from the group consisting of anhydro-daptomycin (FIG. 2), beta-isomer of daptomycin (FIG. 3) and a lactone hydrolysis product of daptomycin (FIG. 4) after storage for 1 month at 40 degrees C. under nitrogen, compared to a solid pharmaceutical daptomycin preparation obtained by lyophilizing daptomycin and daptomycin-related compounds in 0.9% aqueous sodium chloride diluent, where the amount of the substances is detected by HPLC at 214 nm according to the method of Example 4.

Any of the specific embodiments 1-10 can pertain to a solid daptomycin preparation having a Daptomycin Stability Ratio of less than 1.000, less than 0.900, less than 0.800, less than 0.700, less than 0.600, less than 0.500, less than 0.400, less than 0.300, less than 0.200 or less than 0.100, where the Daptomycin Stability Ratio is calculated at 40 degrees C. according to Example 5.

Other compositions include a powder, pharmaceutical composition comprising daptomycin and at least one excipient selected from sorbitol, mannitol, sucrose, glycine, trehalose, lactose, maltose, fructose and dextrose.

The composition of specific embodiment 1 comprising:
a. 500 mg daptomycin;
b. 714.3 mg sucrose; and
c. 35.5 mg sodium phosphate dibasic
wherein the composition is compounded at a pH of about 7.

The composition of specific embodiment 1 comprising:
a. 500 mg daptomycin;
b. 476.2 mg sucrose;
c. 142.9 mg mannitol; and
d. 35.5 mg sodium phosphate dibasic
wherein the composition is compounded at a pH of about 7.

The composition of specific embodiment 1 comprising:
a. 500 mg daptomycin;
b. 476.2 mg sucrose;
c. 285.8 mg mannitol; and
d. 35.5 mg sodium phosphate dibasic
wherein the composition is compounded at a pH of about 7.

In some solid pharmaceutical daptomycin preparations, at least at least 92%, at least 93%, at least 94%, at least 95%, at least 96%, at least 97% or at least 98% by weight of the preparation (e.g., measured upon reconstitution as weight by volume by HPLC according to Example 4) consists of daptomycin and sucrose, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 1 minute at a pH of less than 7.0. In some solid pharmaceutical daptomycin preparations, at least 92%, at least 93%, at least 94%, at least 95%, at least 96%, at least 97% or at least 98% by weight of the preparation (e.g., measured upon reconstitution as weight by volume by HPLC according to Example 4) consists of daptomycin, sucrose and a sodium phosphate buffering agent, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 1 minute at a pH of about 7.0. In one solid pharmaceutical daptomycin preparation, at least 92%, at least 93%, at least 94%, at least 95%, at least 96%, at least 97% or at least 98% by weight of the preparation (e.g., measured upon reconstitution as weight by volume by HPLC according to Example 4) consists of daptomycin, sucrose and a buffering agent, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 1 minute at a pH of about 7.0, and the daptomycin preparation is obtained by converting a daptomycin solution comprising 15-20% w/v sucrose to the daptomycin preparation (e.g., by lyophilization or spray drying). In one solid pharmaceutical daptomycin preparation, at least 92%, at least 93%, at least 94%, at least 95%, at least 96%, at least 97% or at least 98% by weight of the preparation (e.g., measured upon reconstitution as weight by volume by HPLC according to Example 4) consists of daptomycin, sucrose and sodium phosphate dibasic, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 1 minute at a pH of about 7.0, and the daptomycin preparation is obtained by converting a daptomycin solution comprising 15-20% w/v sucrose and 50 mM sodium phosphate dibasic to the daptomycin preparation (e.g., by lyophilization or spray drying).

In some solid pharmaceutical daptomycin preparations, at least 92%, at least 93%, at least 94%, at least 95%, at least 96%, at least 97% or at least 98% of the HPLC peak area detected at 214 nm (measured upon reconstitution as weight by volume by HPLC according to Example 4) is provided by daptomycin, and the composition consists of daptomycin, other materials detected at 214 nm by HPLC according to Example 3, glycine or one or more sugars, and a sodium phosphate buffering agent, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 1 minute at a pH of about 7.0.

In some solid pharmaceutical daptomycin preparations, at least 92%, at least 93%, at least 94%, at least 95%, at least 96%, at least 97% or at least 98% by weight of the preparation (e.g., measured upon reconstitution as weight by volume by HPLC according to Example 4) consists of daptomycin and trehalose, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 1 minute at a pH of less than 7.0. In some solid pharmaceutical daptomycin preparations, at least 92%, at least 93%, at least 94%, at least 95%, at least 96%, at least 97% or at least 98% by weight of the preparation (e.g., measured upon reconstitution as weight by volume by HPLC according to Example 4) consists of daptomycin, trehalose and a sodium phosphate buffering agent, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 1 minute at a pH of about 7.0.

In some solid pharmaceutical daptomycin preparations, at least 92%, at least 93%, at least 94%, at least 95%, at least 96%, at least 97% or at least 98% by weight of the preparation (e.g., measured upon reconstitution as weight by volume by HPLC according to Example 4) consists of daptomycin and glycine, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 1 minute at a pH of less than 7.0.

In some solid pharmaceutical daptomycin preparations, at least 92%, at least 93%, at least 94%, at least 95%, at least 96%, at least 97% or at least 98% by weight of the preparation consists of daptomycin, mannitol, and sucrose, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 1 minute at a pH of less than 7.0. In some solid pharmaceutical daptomycin preparations, at least 92%, at least 93%, at least 94%, at least 95%, at least 96%, at least 97% or at least 98% by weight of the preparation consists of daptomycin, mannitol, sucrose and a sodium phosphate buffering agent, where the pharmaceutical daptomycin preparation is characterized in that about 500 mg of the solid pharmaceutical daptomycin preparation dissolves in about 10 mL of an aqueous diluent (e.g., 0.9% aqueous sodium chloride) in less than about 1 minute at a pH of about 7.0.

Methods of making a daptomycin pharmaceutical composition for parenteral administration are also provided. The method can include reconstituting a solid daptomycin preparation comprising a non-reducing sugar or glycine in a pharmaceutically acceptable diluent to form the composition for parenteral administration.

The compositions of the present invention can be made by a variety of methods. In one aspect, the compositions are made by:
a. supplying a daptomycin preparation
b. adding at least one excipient selected from sorbitol, mannitol, sucrose, glycine, trehalose, lactose, maltose, fructose and dextrose;
c. adding a pH adjuster to obtain the desired pH
d. diluting the solution of step c with sWFI
e. filtering the solution of step d; and
f. converting the composition to a powdered form.

In another aspect of the invention is provided a method for preparing compositions of specific embodiment 1 that are compounded with a buffer, for example at pH 7. This process comprises the steps of
a. supplying a daptomycin preparation
b. adding a pH adjuster to obtain a solution of about pH 4.7-6.0;
c. adding a buffering agent;
d. adding at least one excipient selected from sorbitol, mannitol, sucrose, glycine, trehalose, lactose, maltose, fructose and dextrose;
e. adding a pH adjuster to obtain a pH of about 7.0
f. diluting the bulk solution with sWFI
g. filtering the solution of step f; and
h. converting the composition to a powder form to obtain the solid daptomycin composition.

In another aspect of the invention is provided a method for preparing compositions of specific embodiment 1 that are compounded with a buffer, for example at pH 7. This process comprises the steps of
a. supplying a daptomycin preparation
b. adding a pH adjuster to obtain a solution of about pH 4.7-6.0;
c. adding a buffering agent;
d. adding at least one excipient selected from sorbitol, mannitol, sucrose, glycine, trehalose, lactose, maltose, fructose and dextrose;
e. adding a pH adjuster to obtain a pH of about 7.0
f. diluting the bulk solution with sWFI
g. filtering the solution of step f; and
h. converting the composition to a powder form to obtain the composition of specific embodiment 1.

A number of other embodiments of the invention have been described. Nevertheless, it will be understood that various modifications may be made without departing from the spirit and scope of the invention. Accordingly, other embodiments are within the scope of the following claims.

The invention claimed is:

1. A solid pharmaceutical daptomycin composition, wherein said composition is prepared by lyophilizing an aqueous daptomycin solution comprising daptomycin and sucrose.

2. The solid pharmaceutical daptomycin composition of claim 1, wherein the molar ratio of daptomycin to sucrose is about 1:1.12 to about 1:8.98.

3. The solid pharmaceutical daptomycin composition of claim 1, wherein the aqueous daptomycin solution further comprises a buffering agent.

4. The solid pharmaceutical daptomycin composition of claim 3, wherein the buffering agent is selected from the group consisting of phosphate, citrate, maleate, carbonate, or a combination thereof.

5. The solid pharmaceutical daptomycin composition of claim 3, wherein the buffering agent is selected from the group consisting of sodium phosphate dibasic, sodium citrate, sodium bicarbonate, histidine monohydrochloride, tris(hydroxymethyl)aminomethane, maleate, or a combination thereof.

6. The solid pharmaceutical daptomycin composition of claim 3, wherein the buffering agent is sodium phosphate dibasic.

7. The solid pharmaceutical daptomycin composition of claim 1, wherein the aqueous daptomycin solution has a pH of about 4.5 to about 8.0.

8. The solid pharmaceutical daptomycin composition of claim 7, wherein the aqueous daptomycin solution has a pH of about 6.5 to about 7.5.

9. The solid pharmaceutical daptomycin composition of claim 8, wherein the aqueous daptomycin solution has a pH of about 7.0.

10. A pharmaceutical product comprising the solid pharmaceutical daptomycin composition of claim 1 and a pharmaceutically acceptable diluent.

11. The pharmaceutical product according to claim 10, wherein the pharmaceutically acceptable diluent is selected from sterile water for injection, sterile sodium chloride for injection, or bacteriostatic water for injection.

12. A solid pharmaceutical daptomycin composition, wherein the solid pharmaceutical daptomycin composition is prepared by a process comprising:
  a. forming an aqueous solution comprising daptomycin, wherein the aqueous solution has a pH of about 4.5 to about 5.0;
  b. adding a buffering agent to the aqueous solution of daptomycin;
  c. dissolving sucrose in the aqueous solution of daptomycin to form a buffered daptomycin sucrose formulation;
  d. adjusting the pH of the buffered daptomycin sucrose formulation to about 6.5 to about 7.5; and
  e. converting the buffered daptomycin sugar formulation to the solid pharmaceutical daptomycin composition.

13. The solid pharmaceutical daptomycin composition of claim 12, wherein the buffering agent is selected from the group consisting of phosphate, citrate, maleate, carbonate, or a combination thereof.

14. The solid pharmaceutical daptomycin composition of claim 12, wherein the buffering agent is selected from the group consisting of sodium phosphate dibasic, sodium citrate, sodium bicarbonate, histidine monohydrochloride, tris(hydroxymethyl)aminomethane, maleate, or a combination thereof.

15. A solid pharmaceutical daptomycin composition, wherein the solid pharmaceutical daptomycin composition is prepared by a process comprising:
  a. dissolving sucrose in an aqueous solution comprising daptomycin to form a daptomycin sucrose formulation;
  b. adjusting the pH of the daptomycin sucrose formulation to about 6.5 to about 7.5; and
  c. converting the daptomycin sugar formulation to the solid pharmaceutical daptomycin composition.

* * * * *